United States Patent
Sloey et al.

(10) Patent No.: US 8,383,114 B2
(45) Date of Patent: Feb. 26, 2013

(54) PHARMACEUTICAL FORMULATIONS

(75) Inventors: Christopher J. Sloey, Newbury Park, CA (US); Camille Vergara, Calabasas, CA (US); Jason Ko, Thousand Oaks, CA (US); Tiansheng Li, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/680,128

(22) PCT Filed: Sep. 29, 2008

(86) PCT No.: PCT/US2008/078193
§ 371 (c)(1),
(2), (4) Date: Jul. 12, 2010

(87) PCT Pub. No.: WO2009/043049
PCT Pub. Date: Apr. 2, 2009

(65) Prior Publication Data
US 2010/0297106 A1    Nov. 25, 2010

Related U.S. Application Data

(60) Provisional application No. 60/975,780, filed on Sep. 27, 2007.

(51) Int. Cl.
C07K 14/00    (2006.01)

(52) U.S. Cl. .......... 424/134.1; 514/12; 530/350

(58) Field of Classification Search .......... None
See application file for complete search history.

(56) References Cited

U.S. PATENT DOCUMENTS

| | | |
|---|---|---|
| 4,703,008 A | 10/1987 | Lin |
| 5,441,868 A | 8/1995 | Lin |
| 5,547,933 A | 8/1996 | Lin |
| 5,618,698 A | 4/1997 | Lin |
| 5,621,080 A | 4/1997 | Lin |
| 5,686,292 A | 11/1997 | Schwall et al. |
| 5,756,349 A | 5/1998 | Lin |
| 5,767,078 A | 6/1998 | Johnson et al. |
| 5,773,569 A | 6/1998 | Wrighton et al. |
| 5,789,554 A | 8/1998 | Leung et al. |
| 5,830,851 A | 11/1998 | Wrighton et al. |
| 5,856,298 A | 1/1999 | Strickland |
| 5,955,422 A | 9/1999 | Lin |
| 5,986,047 A | 11/1999 | Wrighton et al. |
| 6,030,086 A | 2/2000 | Thomas |
| 6,310,078 B1 | 10/2001 | Connolly et al. |
| 6,391,633 B1 | 5/2002 | Stern et al. |
| 6,468,529 B1 | 10/2002 | Schwall et al. |
| 6,583,272 B1 | 6/2003 | Bailon |
| 6,586,398 B1 | 7/2003 | Kinstler et al. |
| 6,750,369 B2 | 6/2004 | Connolly et al. |
| 6,756,480 B2 | 6/2004 | Kostenuik et al. |
| 6,803,453 B1 | 10/2004 | Brunkow et al. |
| 6,835,809 B1 | 12/2004 | Liu et al. |
| 6,900,292 B2 | 5/2005 | Sun et al. |
| 6,919,426 B2 | 7/2005 | Boone et al. |
| 7,030,226 B2 | 4/2006 | Sun et al. |
| 7,037,498 B2 | 5/2006 | Cohen et al. |
| 7,084,245 B2 | 8/2006 | Holmes et al. |
| 7,153,507 B2 | 12/2006 | van de Winkel et al. |
| 7,217,689 B1 | 5/2007 | Elliott et al. |
| 7,220,410 B2 | 5/2007 | Kim et al. |
| 2002/0155998 A1 | 10/2002 | Young et al. |
| 2002/0199213 A1 | 12/2002 | Tomizuka et al. |
| 2003/0023586 A1 | 1/2003 | Knorr |
| 2003/0031667 A1 | 2/2003 | Deo et al. |
| 2003/0077753 A1 | 4/2003 | Tischer |
| 2003/0082749 A1 | 5/2003 | Sun et al. |
| 2003/0118592 A1 | 6/2003 | Ledbetter et al. |
| 2003/0133939 A1 | 7/2003 | Ledbetter et al. |
| 2003/0138421 A1 | 7/2003 | van de Winkel et al. |
| 2003/0143202 A1 | 7/2003 | Binley et al. |
| 2003/0194404 A1 | 10/2003 | Greenfeder et al. |
| 2003/0195156 A1 | 10/2003 | Min et al. |
| 2003/0215444 A1 | 11/2003 | Elliott |
| 2003/0229023 A1 | 12/2003 | Oliner et al. |
| 2003/0235582 A1 | 12/2003 | Singh et al. |
| 2004/0009902 A1 | 1/2004 | Boime et al. |
| 2004/0018191 A1 | 1/2004 | Wang et al. |
| 2004/0071694 A1 | 4/2004 | DeVries et al. |
| 2004/0071702 A1 | 4/2004 | van de Winkel et al. |
| 2004/0086503 A1 | 5/2004 | Cohen et al. |
| 2004/0091961 A1 | 5/2004 | Evans et al. |
| 2004/0097712 A1 | 5/2004 | Varnum et al. |
| 2004/0143857 A1 | 7/2004 | Young et al. |
| 2004/0157293 A1 | 8/2004 | Evans et al. |
| 2004/0175379 A1 | 9/2004 | DeVries et al. |

(Continued)

FOREIGN PATENT DOCUMENTS

| | | |
|---|---|---|
| EP | 404097 A2 | 12/1990 |
| EP | 1188445 A1 | 3/2002 |

(Continued)

OTHER PUBLICATIONS

Altschul et al., "Basic Local Alignment Research Tool", J Mol Biol 215: 403-410 (1990).
Biocca, et al., "Expression and targeting of intracellular antibodies in mammalian cells," EMBO J. 9:101-108, 1990.
Bird et al., "Single-Chain Antigen-Binding Proteins," Science 242:423-426, (1988).
Bruggermann et al., "Designer Mice: The Production of Human Antibody Repertoires in Transgenic Animals,"Year in Immuno., 7:33 (1993).
Caton and Koprowski, "Influenza virus hemagglutinin-specific antibodies isolated from a combinatorial expression library are closely related to the immune response of the donor," Proc. Natl. Acad. Sci. USA, 87:6450-6454 1990.
Chothia et al., "Canonical Structures for the Hypervariable Regions of Immunoglobulins," J. Mol.Biol. 196: 901-917 (1987).
Co, et al., "A Humanized Antibody Specific for the Platelet Integrin gpllb/llla," J. Immunol. 152, 2968-2976 (1994).
Cohen, et al., "Combination Therapy Enhances the Inhibition of Tumor Growth with the Fully Human Anti-Type 1 Insulin-Like Growth Factor Receptor Monoclonal Antibody CP-751,871," Clinical Cancer Res. 11:2063-73 (2005).

(Continued)

*Primary Examiner* — Yunsoo Kim
(74) *Attorney, Agent, or Firm* — Marshall, Gerstein & Borun LLP

(57) ABSTRACT

A stable pharmaceutical formulation is provided that comprises a biologically active protein and an excipient selected from carnitine, creatine or creatinine.

6 Claims, 12 Drawing Sheets

U.S. PATENT DOCUMENTS

| | | | |
|---|---|---|---|
| 2004/0175824 A1 | 9/2004 | Sun et al. | |
| 2004/0181033 A1 | 9/2004 | Han et al. | |
| 2004/0197324 A1* | 10/2004 | Liu et al. | 424/130.1 |
| 2004/0202655 A1 | 10/2004 | Morton et al. | |
| 2004/0228859 A1 | 11/2004 | Graus et al. | |
| 2004/0229318 A1 | 11/2004 | Heavner | |
| 2004/0248815 A1 | 12/2004 | Connolly et al. | |
| 2004/0265307 A1 | 12/2004 | Singh et al. | |
| 2004/0266690 A1 | 12/2004 | Pool | |
| 2005/0004353 A1 | 1/2005 | Welcher et al. | |
| 2005/0008642 A1 | 1/2005 | Graus et al. | |
| 2005/0019914 A1 | 1/2005 | Staerk et al. | |
| 2005/0026834 A1 | 2/2005 | Cox et al. | |
| 2005/0037421 A1 | 2/2005 | Honda et al. | |
| 2005/0074821 A1 | 4/2005 | Wild et al. | |
| 2005/0084906 A1 | 4/2005 | Goetsch et al. | |
| 2005/0089932 A1 | 4/2005 | Kolkman et al. | |
| 2005/0096461 A1 | 5/2005 | Cox | |
| 2005/0107297 A1 | 5/2005 | Holmes et al. | |
| 2005/0107591 A1 | 5/2005 | Cox | |
| 2005/0112694 A1 | 5/2005 | Carter et al. | |
| 2005/0118643 A1 | 6/2005 | Burgess et al. | |
| 2005/0124045 A1 | 6/2005 | Sun et al. | |
| 2005/0124564 A1 | 6/2005 | Binley et al. | |
| 2005/0136049 A1 | 6/2005 | Ledbetter et al. | |
| 2005/0136063 A1 | 6/2005 | Wang et al. | |
| 2005/0137329 A1 | 6/2005 | Holmes et al. | |
| 2005/0142642 A1 | 6/2005 | Sun et al. | |
| 2005/0143292 A1 | 6/2005 | DeFrees et al. | |
| 2005/0153879 A1 | 7/2005 | Svetina et al. | |
| 2005/0158822 A1 | 7/2005 | Pecker | |
| 2005/0158832 A1 | 7/2005 | Young et al. | |
| 2005/0170457 A1 | 8/2005 | Pool et al. | |
| 2005/0181359 A1 | 8/2005 | Optelten et al. | |
| 2005/0181482 A1 | 8/2005 | Meade et al. | |
| 2005/0186203 A1 | 8/2005 | Singh et al. | |
| 2005/0192211 A1 | 9/2005 | Gillies et al. | |
| 2005/0202538 A1 | 9/2005 | Gillies et al. | |
| 2005/0227289 A1 | 10/2005 | Reilly et al. | |
| 2005/0244408 A1 | 11/2005 | Cohen et al. | |
| 2005/0244409 A1 | 11/2005 | Erickson-Miller et al. | |
| 2005/0249728 A1 | 11/2005 | Singh et al. | |
| 2006/0040358 A1 | 2/2006 | Ligensa et al. | |
| 2006/0040858 A1 | 2/2006 | Holmes et al. | |
| 2006/0088906 A1 | 4/2006 | DeFrees et al. | |
| 2006/0111279 A1 | 5/2006 | DeFrees et al. | |
| 2006/0135431 A1 | 6/2006 | Min et al. | |
| 2007/0110747 A1 | 5/2007 | Paszty et al. | |

FOREIGN PATENT DOCUMENTS

| | | |
|---|---|---|
| WO | WO-90/00397 A1 | 1/1990 |
| WO | WO-91/10741 A1 | 7/1991 |
| WO | WO-91/17271 A1 | 11/1991 |
| WO | WO-92/01047 A1 | 1/1992 |
| WO | WO-93/11161 A1 | 6/1993 |
| WO | WO-95/05465 A1 | 2/1995 |
| WO | WO-96/34096 A1 | 10/1996 |
| WO | WO 96/38557 A1 | 12/1996 |
| WO | WO-99/66054 A2 | 12/1999 |
| WO | WO-00/24782 A2 | 5/2000 |
| WO | WO-00/24893 A2 | 5/2000 |
| WO | WO-00/61637 A1 | 10/2000 |
| WO | WO-01/28360 A1 | 4/2001 |
| WO | WO-01/36489 A2 | 5/2001 |
| WO | WO-01/81405 A2 | 11/2001 |
| WO | WO-02/014356 A2 | 2/2002 |
| WO | WO-02/19963 A2 | 3/2002 |
| WO | WO-02/20034 A1 | 3/2002 |
| WO | WO-91/05867 A1 | 5/2002 |
| WO | WO-02/49673 A2 | 6/2002 |
| WO | WO-02/085940 A2 | 10/2002 |
| WO | WO-03/002713 A2 | 1/2003 |
| WO | WO-03/029291 A2 | 4/2003 |
| WO | WO-03/030833 A2 | 4/2003 |
| WO | WO-03/041600 A1 | 5/2003 |
| WO | WO-03/055526 A2 | 7/2003 |
| WO | WO-03/057134 A2 | 7/2003 |
| WO | WO-03/059951 A2 | 7/2003 |
| WO | WO-03/084477 A2 | 10/2003 |
| WO | WO-03/094858 A2 | 11/2003 |
| WO | WO-2004/002417 A2 | 1/2004 |
| WO | WO-2004/002424 A2 | 1/2004 |
| WO | WO-2004/009627 A1 | 1/2004 |
| WO | WO-2004/018667 A1 | 3/2004 |
| WO | WO-2004/024761 A1 | 3/2004 |
| WO | WO-2004/033651 A2 | 4/2004 |
| WO | WO-2004/035603 A2 | 4/2004 |
| WO | WO-2004/043382 A2 | 5/2004 |
| WO | WO-2004/058988 A2 | 7/2004 |
| WO | WO-2004/073092 A2 | 8/2004 |
| WO | WO-2004/101600 A2 | 11/2004 |
| WO | WO-2004/101606 A2 | 11/2004 |
| WO | WO-2004/101611 A2 | 11/2004 |
| WO | WO-2004/106373 A1 | 12/2004 |
| WO | WO-2005/001025 A2 | 1/2005 |
| WO | WO-2005/001136 A1 | 1/2005 |
| WO | WO-2005/016970 A2 | 2/2005 |
| WO | WO-2005/017107 A2 | 2/2005 |
| WO | WO-2005/021579 A2 | 3/2005 |
| WO | WO-2005/025606 A1 | 3/2005 |
| WO | WO-2005/032460 A2 | 4/2005 |
| WO | WO-2005/047331 A2 | 5/2005 |
| WO | WO-2005/051327 A2 | 6/2005 |
| WO | WO-2005/058967 A2 | 6/2005 |
| WO | WO-2005/063808 A1 | 7/2005 |
| WO | WO-2005/063809 A1 | 7/2005 |
| WO | WO-2005/070451 A1 | 8/2005 |
| WO | WO-2005/081687 A2 | 9/2005 |
| WO | WO-2005/084711 A1 | 9/2005 |
| WO | WO-2005/092369 A2 | 10/2005 |
| WO | WO-2005/100403 A2 | 10/2005 |
| WO | WO-2005/103076 A2 | 11/2005 |
| WO | WO 2006/02646 A2 | 1/2006 |
| WO | WO-2006/013472 A2 | 2/2006 |
| WO | WO-2006/29094 A2 | 3/2006 |
| WO | WO-2006/50959 A2 | 5/2006 |
| WO | WO-2006/069202 A2 | 6/2006 |
| WO | WO-2006081171 A1 | 8/2006 |
| WO | WO-2006/138729 A2 | 12/2006 |
| WO | WO-2007/000328 A1 | 1/2007 |
| WO | WO-2007/011941 A2 | 1/2007 |
| WO | WO-2007/012614 A2 | 2/2007 |
| WO | WO-2007/057748 A2 | 5/2007 |
| WO | WO-98/24893 A2 | 6/2011 |

OTHER PUBLICATIONS

Colby et al., "Potent inhibition of huntingtin aggregation and cytotoxicity by a disulfide bond-free single-domain intracellular antibody," Proc Natl Acad Sci U S A. 101:17616-21, 2004.

Cortez-Retamozo et al., "Efficient Cancer Therapy with a Nanobody-Based Conjugate," Cancer Research 64:2853-57, 2004.

Desmyter et al., "Antigen Specificity and High Affinity Binding Provided by One Single Loop of a Camel Single-domain Antibody," J. Biol. Chem. 276:26285-90, 2001.

Doolittle, R. F.: "Searching through sequence databases," Met Enz. 183: 99-110 (1990).

Ewert et al., "Biophysical Properties of Camelid $V_{HH}$ Domains Compared to Those of Human $V_H$3 Domains," Biochemistry 41:3628-36, 2002.

Gill et al., "Biopharmaceutical drug discovery using novel protein scaffolds," Current Opin. Biotechnol., 17:653-658 (2006).

Gruber et al., "Efficient Tumor Cell Lysis Mediated by a Bispecific Single Chain Antibody Expressed in *Escherichia coli*," J. Immunol. 152: 5368 (1994).

Heng et al., "Making cell-permeable antibodies (Transbody) through fusion of protein transduction domains (PTD) with single chain variable fragment (scFv) antibodies: Potential advantages over antibodies expressed within the intracellular environment (Intrabody)," Med Hypotheses. 64:1105-8, 2005.

Hollinger et al., "Diabodies: Small bivalent and bispecific antibody fragments," Proc. Natl. Acad. Sci. USA, 90:6444-6448 (1993).

Hosse et al., "A new generation of protein display scaffolds for molecular recognition," Protein Science 15:14-27, 2006.

Huston et al., "Protein engineering of antibody binding sites: Recovery of specific activity in an anti-digoxin single-chain Fv analogue produced in *Escherichia coli*," Proc. Natl. Acad. Sci. USA 85:5879-5883, 1988.

International Search Report from PCT/US2008/078193 dated Mar. 4, 2010.

Jakobovits et al., "Germ-line transmission and expression of a human-derived yeast artifical chromosome," Nature, 362:255-258 (1993).

Jakobovits et al., "Analysis of homozygous mutant chimeric mice: Deletion of the immunoglobulin heavy-chain joining region blocks B-cell development and antibody production," Proc. Natl. Acad. Sci. USA, 90:2551 (1993).

Jones et al., "Replacing the complementarity-determining regions in a human antibody with those from a mouse," Nature 321:522 525 (1986).

Kettleborough, et al., "Humanization of a mouse monoclonal antibody by CDR-grafting: the importance of framework residues on loop conformation," Protein Eng. 4 (7):773 83 (1991).

Kostelny et al., "Formation of a Bispecific Antibody by the Use of Leucine Zippers," J. Immunol. 148:1547-1553, 1992.

Lu et al., "Simultaneous Blockade of Both the Epidermal Growth Factor Receptor and the Insulin-like Growth Factor Receptor Signaling Pathways in Cancer Cells with a Fully Human Recombinant Bispecific Antibody," J Biol Chem. 279:2856-65 (2004).

Maloney et al., "An Anti-Insulin-like Growth Factor I Receptor Antibody that is a Potent Inhibitor of Cancer Cell Proliferation," Cancer Res. 63:5073-83 (2003).

Mhashilkar et al, "Inhibition of HIV-1 Tat-mediated LTR transactivation and HIV-1 infection by anti-Tat single chain intrabodies," EMBO J 14:1542-51, 1995.

Morrison, et al., "Genetically Engineered Antibody Molecules," Adv. Immunol., 44:65 92 (1988).

Morrison et al., "Chimeric human antibody molecules: Mouse antigen-binding domains with human constant region domains," Proc. Natl. Acad. Sci., U.S.A., 81:6851 6855 (1984).

Myers and Miller: "Optimal alignments in linear space" Comput. Applica. in Biosci 4: 11-17 (1988).

Needleman and Wunsch: "A general method applicable to the search for similarities in amino acid sequence of two proteins," J Mol Biol 48: 443-453 (1970).

Neri et al., "High-affinity Antigen Binding by Chelating Recombinant Antibodies (CRAbs)," J Mol Biol. 246:367-73, 1995.

Olafsen, et al., "Characterization of engineered anti-p185$^{HER-2}$ (scFv-$C_H$3)$_2$ antibody fragments (minibodies) for tumor targeting," Protein Eng Des Sel. Apr. 17(4):315-23 (2004).

Padlan, "A Possible Procedure for Reducing the Immunogenicity of Antibody Variable Domains While Preserving Their Ligand-Binding Properties," Molec. lmmun. 28:489 498 (1991).

Padlan, "Anatomy of the Antibody Molecule," Molec. Immunol. 31(3):169 217 (1994).

Razeghifard et al., "Creating Functional Artificial Proteins," Current Protein & Peptide Science. 8(1):3-18, 2007.

Schoonjans et al., "Fab Chains as an Efficient Heterodimerization Scaffold for the Production of Recombinant Bispecific and Trispecific Antibody Derivatives," J Immunol. 165:7050-57, 2000.

Shields et al., "High Resolution Mapping of the Binding Site on Human IgG1 for FcγRI, FcγRIII, and FcRn and Design of IgG1 Variants with Improved Binding to the FcγR," J. Biol. Chem., 276(9):6591-6604 (2001).

Silverman et al., "Multivalent avimer proteins evolved by exon shuffling of a family of human receptor domains," Nat Biotech 23(12): 1556-1561 (2005).

Skerra, "Engineered protein scaffolds for molecular recognition," J. Mol. Recognit., 13:167-187 (2000).

Studnicka et al. "Human-engineered monoclonal antibodies retain full specific binding activity by preserving non-CDR complementarity-modulating residues," Protein Engineering 7: 805-814 (1994).

Thakur et al., "A potent neutralizing monoclonal antibody can discriminate amongst IFNγ from various primates with greater specificity than can the human IFNγ receptor complex," Mol. Immunol. 36:1107-1115 (1999).

Verhoeyer et al., "Reshaping Human Antibodies: Grafting an Antilysozyme Activity," Science 239:1534 1536 (1988).

Ward et al., "Binding activities of a repertoire of single immunoglobulin variable domains secreted from *Escherichia coli*," Nature 341:544-546, 1989.

Wheeler et al., "Intrabody-based strategies for inhibition of vascular endothelial growth factor receptor-2: effects on apoptosis, cell growth, and angiogenesis," FASEB J. 17:1733-5, 2003.

Willems et al., "Optimizing expression and purification from cell culture medium of trispecific recombinant antibody derivatives," J Chromatogr B Analyt Technol Biomed Life Sci. 786:161-76, 2003).

Wyss, et al., "Creatine and Creatinine Metabolism," Physiol. Rev., vol. 80, No. 3, pp. 1107-1213 (2000).

Zapata et al., "Engineering linear F(ab')$_2$ fragments for efficient production in *Escherichia coli* and enhanced antiproliferative activity," Protein Eng.,8(10):1057-1062 (1995).

* cited by examiner

SEQUENCE LISTING

<160> NUMBER OF SEQ ID NOS: 2

<210> SEQ ID NO 1
<211> LENGTH: 193
<212> TYPE: PRT
<213> ORGANISM: Homo sapiens

```
<220> FEATURE:
<221> NAME/KEY: mat_peptide
<222> LOCATION: (28)..(192)

<400> SEQUENCE: 1

Met Gly Val His Glu Cys Pro Ala Trp Leu Trp Leu Leu Leu Ser Leu
        -25                 -20                 -15

Leu Ser Leu Pro Leu Gly Leu Pro Val Leu Gly Ala Pro Pro Arg Leu
        -10                  -5          -1   1                5

Ile Cys Asp Ser Arg Val Leu Glu Arg Tyr Leu Leu Glu Ala Lys Glu
                10                  15                  20

Ala Glu Asn Ile Thr Thr Gly Cys Ala Glu His Cys Ser Leu Asn Glu
            25                  30                  35

Asn Ile Thr Val Pro Asp Thr Lys Val Asn Phe Tyr Ala Trp Lys Arg
        40                  45                  50

Met Glu Val Gly Gln Gln Ala Val Glu Val Trp Gln Gly Leu Ala Leu
        55                  60                  65

Leu Ser Glu Ala Val Leu Arg Gly Gln Ala Leu Leu Val Asn Ser Ser
70                  75                  80                  85

Gln Pro Trp Glu Pro Leu Gln Leu His Val Asp Lys Ala Val Ser Gly
                90                  95                  100

Leu Arg Ser Leu Thr Thr Leu Leu Arg Ala Leu Gly Ala Gln Lys Glu
            105                 110                 115

Ala Ile Ser Pro Pro Asp Ala Ala Ser Ala Ala Pro Leu Arg Thr Ile
        120                 125                 130

Thr Ala Asp Thr Phe Arg Lys Leu Phe Arg Val Tyr Ser Asn Phe Leu
        135                 140                 145

Arg Gly Lys Leu Lys Leu Tyr Thr Gly Glu Ala Cys Arg Thr Gly Asp
150                 155                 160                 165

Arg

<210> SEQ ID NO 2
<211> LENGTH: 193
<212> TYPE: PRT
<213> ORGANISM: Homo sapiens
<220> FEATURE:
<221> NAME/KEY: mat_peptide
<222> LOCATION: (28)..(192)

<400> SEQUENCE: 2

Met Gly Val His Glu Cys Pro Ala Trp Leu Trp Leu Leu Leu Ser Leu
        -25                 -20                 -15

Leu Ser Leu Pro Leu Gly Leu Pro Val Leu Gly Ala Pro Pro Arg Leu
        -10                  -5          -1   1                5

Ile Cys Asp Ser Arg Val Leu Glu Arg Tyr Leu Leu Glu Ala Lys Glu
                10                  15                  20

Ala Glu Asn Ile Thr Thr Gly Cys Asn Glu Thr Cys Ser Leu Asn Glu
            25                  30                  35

Asn Ile Thr Val Pro Asp Thr Lys Val Asn Phe Tyr Ala Trp Lys Arg
        40                  45                  50

Met Glu Val Gly Gln Gln Ala Val Glu Val Trp Gln Gly Leu Ala Leu
        55                  60                  65

Leu Ser Glu Ala Val Leu Arg Gly Gln Ala Leu Leu Val Asn Ser Ser
70                  75                  80                  85

Gln Val Asn Glu Thr Leu Gln Leu His Val Asp Lys Ala Val Ser Gly
                90                  95                  100

Leu Arg Ser Leu Thr Thr Leu Leu Arg Ala Leu Gly Ala Gln Lys Glu
```

-continued

```
            105                 110                 115
Ala Ile Ser Pro Pro Asp Ala Ala Ser Ala Ala Pro Leu Arg Thr Ile
        120                 125                 130

Thr Ala Asp Thr Phe Arg Lys Leu Phe Arg Val Tyr Ser Asn Phe Leu
    135                 140                 145

Arg Gly Lys Leu Lys Leu Tyr Thr Gly Glu Ala Cys Arg Thr Gly Asp
150                 155                 160                 165

Arg
```

PHARMACEUTICAL FORMULATIONS

CROSS-REFERENCE TO RELATED APPLICATION

This application claims the benefit of prior U.S. provisional application No. 60/975,780 filed Sep. 27, 2007, hereby incorporated by reference in its entirety.

FIELD OF THE INVENTION

The invention relates to pharmaceutical formulations of proteins that contain creatine/creatinine or carnitine.

BACKGROUND

Pharmaceutically active antibodies and other proteins are frequently formulated in liquid solutions, particularly for parenteral injection. The pharmaceutical composition may be sold commercially in a ready-to-use solution form or may be provided in a lyophilized form that is reconstituted with a liquid solution. Additional agents are often included in the protein solution to minimize degradation, precipitation and/or aggregation of the protein. Highly concentrated protein formulations are desirable when delivery of a therapeutic protein in small amounts of volume is required, e.g. during subcutaneous injection. However, highly concentrated protein solutions often exhibit increased viscosity. There exists a need to develop methods of reducing the viscosity of a formulation containing high concentrations of protein, and a need for resulting reduced viscosity formulations.

Creatine (also known as N-amidinosarcosine or (alpha-methylguanido)acetic acid) is a naturally occurring compound that is used by vertebrates for the purpose of energy storage in muscle cells. It is produced by the liver and kidneys and is present in meat and fish in high quantities. It is present in low amounts in blood and is converted in aqueous solutions to creatinine in a reversible reaction. The equilibrium ratio of creatine to creatinine (2-amino-1-methyl-2-imidazolin-4-one) depends on the pH of the solution and will be shifted towards creatinine formation at low pH.

Carnitine (also known as beta-hydroxy-gamma-(trimethylammonio)butyrate) is a metabolic co-factor that is essential for fatty acid metabolism in humans and other organisms. It is present in high amounts in meats and dairy products and in lower quantities in nuts, seeds, vegetables, fruits, and cereals.

SUMMARY OF THE INVENTION

The invention is directed toward formulations, including aqueous solutions or lyophilized powders, containing a therapeutic protein and an excipient selected from the group consisting of creatinine, creatine, carnitine, or mixtures thereof. Guanidinoacetic acid is another excipient that can be used according to the present invention; it can be used in any of the formulations and methods of the present invention, in the same way and at similar concentrations as creatine or creatinine. These formulations of the invention exhibit advantageous properties of reduced viscosity and/or reduced aggregation, particularly at high protein concentrations, e.g., greater than 70 mg/ml, or greater than 100 mg/ml. The formulations of the present invention may be sterile and in a form suitable for parenteral administration, e.g. intravenous or subcutaneous administration. The invention is also directed toward methods of using an excipient selected from the group consisting of creatinine, creatine or carnitine, or mixtures thereof, to stabilize or reduce viscosity of a pharmaceutical formulation of a therapeutic protein. The methods involve combining stabilizing or viscosity-reducing amounts of an excipient selected from the group consisting of creatinine, creatine or carnitine, or mixtures thereof, with the therapeutic protein in an aqueous solution. A variety of therapeutic proteins are contemplated for use in the methods and formulations of the invention, including antibodies and other non-antibody proteins.

In one aspect, the present invention provides a method of reducing the viscosity of a liquid pharmaceutical formulation of an therapeutic protein, by combining a therapeutic protein and a viscosity-reducing amount of an excipient selected from the group consisting of creatinine, creatine or carnitine, or mixtures thereof. In exemplary embodiments, the therapeutic protein is at a concentration of at least about 70 mg/ml, or at least about 100 mg/ml. In some embodiments, the reduction in viscosity is at least about 10%, 20%, or 30% compared to excipient-free controls. The invention also provides formulations produced by such methods.

In yet another aspect, the invention provides liquid solutions comprising a therapeutic protein and an excipient selected from the group consisting of creatinine, creatine or carnitine, or mixtures thereof, wherein the formulations exhibit reduced viscosity or improved stability relative to excipient-free controls. In some embodiments, the excipient is present at a viscosity-reducing (weight:volume) concentration; in other embodiments, the excipient is present at an aggregation-reducing concentration. In exemplary embodiments, the concentration of creatine/creatinine is about 0.002 mM to about 750 mM, or about 0.01 to about 50 mM. In other exemplary embodiments, the concentration of carnitine is about 1 mM to about 3 M, or about 5 to about 300 mM.

In some embodiments, the pH of the composition is between about 4 to 6, or about 5.0-5.5.

In another aspect, the invention provides a method of preparing a lyophilized powder comprising the step of lyophilizing any of the pharmaceutical formulations described herein. In a related aspect, the invention provides lyophilized protein formulations comprising a therapeutic protein and an excipient selected from the group consisting of creatinine, creatine or carnitine, or mixtures thereof, wherein upon reconstitution with the recommended amount of diluent, the formulations exhibit reduced viscosity relative to excipient-free controls. In some embodiments, the excipient is present at a viscosity-reducing (weight:weight) concentration. In exemplary embodiments, the concentration of creatine/creatinine is about 4 ng per mg therapeutic protein to about 1.25 mg per mg therapeutic protein. In other exemplary embodiments, the concentration of carnitine is about 2 µg to about 7 mg per mg therapeutic protein. In other related aspects, the invention provides a method for reconstituting such a lyophilized powder comprising the step of adding a sterile aqueous diluent in the amount recommended by the package label.

In yet another embodiment, the invention provides a method for the administration to a human of the formulations of the invention, including any of the liquid or reconstituted formulations described herein. The invention also provides a method for the treatment, prophylactic or therapeutic, of a disorder treatable by the therapeutic protein (e.g., antibody) that is formulated using the formulations disclosed herein. Such formulations are particularly useful for subcutaneous administration where small volumes, e.g., 1 or 1.5 ml, are desired.

The invention also provides a kit comprising a liquid protein formulation of the invention, and instructions for its administration, optionally with a syringe or other administration device. The invention further provides a kit comprising a lyophilized protein formulation of the invention and instructions for its reconstitution and administration, optionally with a vial of sterile diluent, and optionally with a syringe or other administration device.

In another aspect, a method is disclosed for screening for a viscosity-reducing concentration of excipient selected from the group consisting of creatinine, creatine or carnitine, or mixtures thereof, comprising the steps of: (1) assessing the viscosity of a first solution comprising a first concentration of excipient(s) and a therapeutic protein, such as an antibody, (2) assessing the viscosity of a second solution comprising a different second concentration of excipient(s) and the therapeutic protein, and (3) determining that the first concentration of excipient(s) is more viscosity-reducing than the second concentration of excipient(s) if the first solution is less viscous.

DETAILED DESCRIPTION OF THE INVENTION

Figure 1:
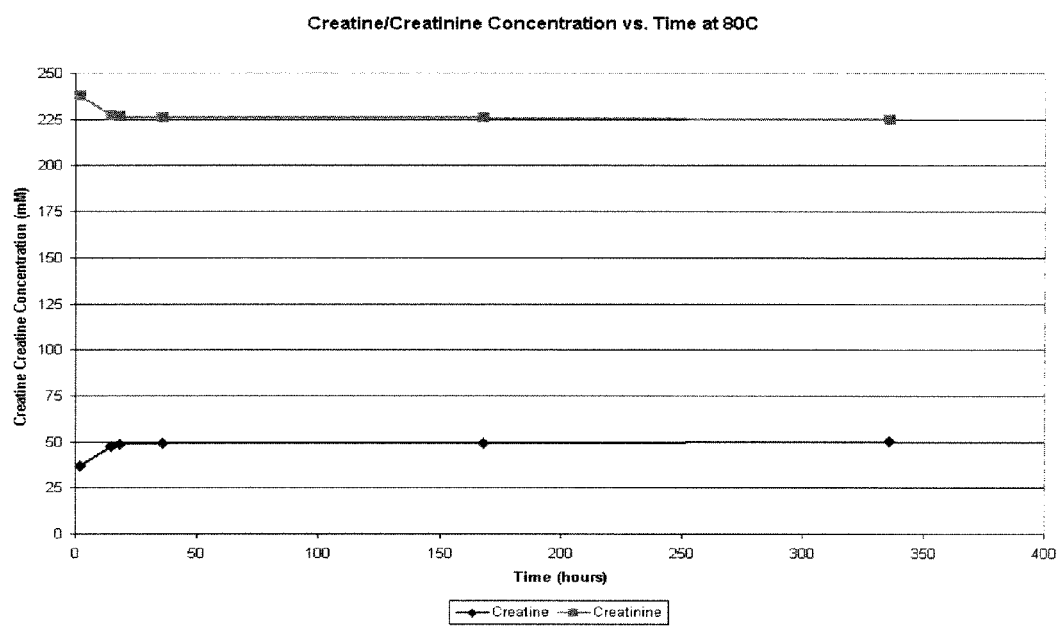
FIG. 1. Preparation of formulations using equilibrium concentrations of creatine/creatine result in stable excipient concentrations during shelf life of antibody formulation.

I. Definitions
A. General
The structures of creatine, creatinine and carnitine are set forth below:

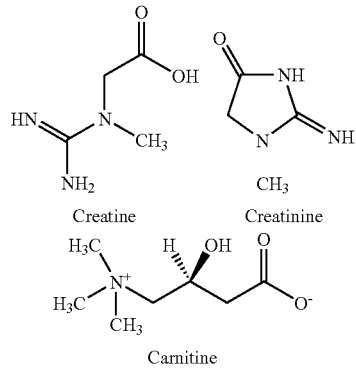

Creatine   Creatinine

Carnitine

The term "antibody" is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab', F'(ab)2, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes have antibody-dependent cellular cytotoxicity (ADCC) activity. An antibody that "specifically binds to" or is "specific for" a particular polypeptide or an epitope on a particular polypeptide is one that binds to that particular polypeptide or epitope on a particular polypeptide without substantially binding to other related polypeptides or polypeptide epitopes.

The term "carnitine" as used herein includes any one of L-carnitine and/or acetyl-L-carnitine; D-carnitine and/or acetyl-D-carnitine; or mixtures of any of the foregoing such as racemic mixtures.

As used herein, the "concentration of creatine/creatinine" will be understood to be the concentration of creatine and creatinine added together. Creatine naturally undergoes a reversible cyclization/dehydration reaction to form creatinine (see, e.g., M. Wyss & R. Kaddurah-Daouk, Physiol. Rev., vol. 80, no. 3, pp. 1107-1213, 2000, incorporated herein by reference in its entirety). This reaction is spontaneous and does not require the presence of an enzyme or catalyst. Conditions of high pH favor creatine, while conditions of low pH favor creatinine. Thus, the term "concentration of creatine/creatinine" refers to the concentrations of creatine and creatinine that would naturally be present under any particular conditions (e.g., pH, temperature) if the recited concentration of either creatine alone, creatinine alone, or a mixture of both, were initially added to the solution. For example, a concentration of 50 mM creatine and 50 mM creatinine would be considered to be 100 mM concentration of creatine/creatinine.

Creatine and creatinine can be separated, identified, and quantitated using a variety of methods known in the art. For example, a reverse-phase chromatography method (RP-HPLC) can involve isocratic elution of the compounds in a mobile phase containing 0.045 M ammonium sulfate from a C18 reverse-phase column followed by detection of the compounds at 205 nM using a UV detector. The integration of the respective peaks allows for relative quantitation of creatine and creatinine as well as absolute quantitation using a standard curve of known injected quantities. The identities of suspected creatine and creatinine peaks can be confirmed with direct mass spectrometry detection (LC-MS). Alternatively, fractions corresponding to the suspected peaks can be collected and further analyzed by mass spectrometry, vibrational spectroscopy, or other chemical tests for identification of creatine and creatinine. Quantitation using RP-HPLC/LC-MS, for example, is expected to be better than other methods such as Fourier Transform Infrared (FTIR) or Raman spectroscopy.

As used herein, "pharmaceutical formulation" is a sterile composition of a pharmaceutically active drug, such as a biologically active protein, that is suitable for parenteral administration (including but not limited to intravenous, intramuscular, subcutaneous, aerosolized, intrapulmonary, intranasal or intrathecal) to a patient in need thereof and includes only pharmaceutically acceptable excipients, diluents, and other additives deemed safe by the Federal Drug Administration or other foreign national authorities. Pharmaceutical formulations include liquid, e.g. aqueous, solutions that may be directly administered, and lyophilized powders which may be reconstituted into solutions by adding a diluent before administration. Specifically excluded from the scope of the term "pharmaceutical formulation" are compositions for topical administration to patients, compositions for oral ingestion, and compositions for parenteral feeding.

As used herein, "shelf life" means that the storage period during which an active ingredient such as a therapeutic protein in a pharmaceutical formulation has minimal degradation (e.g., not more than about 2-3% degradation) when the pharmaceutical formulation is stored under specified storage conditions, for example, 2-8° C. Techniques for assessing degradation vary depending upon the identity of the protein in the pharmaceutical formulation. Exemplary techniques include size-exclusion chromatography (SEC)-HPLC to detect, e.g., aggregation, reverse phase (RP)-HPLC to detect, e.g. protein fragmentation, ion exchange-HPLC to detect, e.g., changes in the charge of the protein, mass spectrometry, fluorescence spectroscopy, circular dichroism (CD) spectroscopy, Fourier transform infrared spectroscopy (FT-IR), and Raman spectroscopy to detect protein conformational changes. All of these techniques can be used singly or in combination to assess the degradation of the protein in the pharmaceutical formulation and determine the shelf life of that formulation. The pharmaceutical formulations of the present invention preferably exhibit degradation (e.g., fragmentation, aggregation or unfolding) of not more than about 2 to about 3% over two years when stored at 2-8° C.

As used herein, "stable" formulations of biologically active proteins are formulations that exhibit reduced aggregation and/or reduced loss of biological activity of at least 5% upon storage at 2-8 degrees Centigrade for at least 2 years compared with a control sample, or alternatively which exhibit reduced aggregation and/or reduced loss of biological activity under conditions of thermal stress, e.g. 52 degrees Centigrade for 7-8 days.

As used herein, "viscosity" is a fluid's resistance to flow, and may be measured in units of centipoise (cP) or milliPascal-second (mPa-s), where 1 cP=1 mPa-s, at a given shear rate. Viscosity may be measured by using a viscometer, e.g., Brookfield Engineering Dial Reading Viscometer, model LVT. Viscosity may be measured using any other methods and in any other units known in the art (e.g. absolute, kinematic or dynamic viscosity), understanding that it is the percent reduction in viscosity afforded by use of the excipients described by the invention that is important. Regardless of the method used to determine viscosity, the percent reduction in viscosity in excipient versus control will remain approximately the same at a given shear rate.

As used herein, a formulation containing an amount of excipient effective to "reduce viscosity" (or a "viscosity-reducing" amount or concentration of such excipient) means that the viscosity of the formulation in its final form for administration (if a solution, or if a powder, upon reconstitution with the intended amount of diluent) is at least 5% less than the viscosity of a control formulation lacking such excipient ("excipient-free"). Similarly, a "reduced viscosity" formulation is a formulation that exhibits reduced viscosity compared to an excipient-free formulation.

Therapeutic Proteins

The terms "polypeptide" and "protein" are used interchangeably herein, and refer to a polypeptide having a molecular weight of at least about 4 kilodaltons (kD). Exemplary polypeptides may have a molecular weight of at least about 4 kD, 8 kD, 15 kD, 20 kD, 25 kD, 30 kD, 40 kD or 50 kD.

The invention herein disclosed may be practiced with a variety of proteins as herein described. Among exemplary proteins in this regard are pharmaceutical proteins for veterinary and/or human therapeutic use, particularly proteins for human therapeutic use. Also among exemplary proteins are proteins that are soluble in aqueous solutions, particularly those that are soluble at relatively high concentrations and those that are stable for long periods of time.

Among the variety of pharmaceutically active proteins contemplated for use in the formulations and methods of the invention are antibodies, peptibodies, immunoglobulin-like proteins, non-antibody proteins, non-immunoglobulin-like proteins, fusion proteins such as peptibodies, Fc-fusion proteins, avimers, chimeric proteins, and/or multi-chain proteins, whether naturally occurring or non-naturally occurring. Nonlimiting examples include structural proteins, enzymes, hormones, hematopoietic factors, growth factors, cytokines, chemokines, antiobesity factors, trophic factors, anti-inflammatory factors and regulatory proteins, including but not limited to stem cell factor, leptin, insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferon (alpha, beta, gamma), interleukin (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), bone growth factor such as osteoprotegerin (OPG), insulin-like growth factor (IGF), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factor (CSF), bone morphogenetic protein (BMP), superoxide dismutase (SOD), tissue plasminogen activator (TPA), urokinase, streptokinase, or kallikrein. Analogs of naturally occurring proteins are contemplated for use in formulations and methods of the present invention, including polypeptides with modified glycosylation, or polypeptides without glycosylation (unglycosylated), and polypeptides with other post-translational modifications which may be made by cellular modification systems or via enzymatic and/or chemical methods.

In some embodiments, the therapeutic protein is an erythropoiesis stimulating protein. As used herein, "erythropoiesis stimulating protein" means a protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Patent Application Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; 7,217,689; PCT publication nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; WO 2006/29094; and US publication nos. US 2002/0155998; US 2003/0077753; US 2003/0082749; US 2003/0143202; US 2004/0009902; US 2004/0071694; US 2004/0091961; US 2004/0143857; US 2004/0157293; US 2004/0175379; US 2004/0175824; US 2004/0229318; US 2004/0248815; US 2004/0266690; US 2005/0019914; US 2005/0026834; US 2005/0096461; US 2005/0107297; US 2005/0107591; US 2005/0124045; US 2005/0124564; US 2005/0137329; US 2005/0142642; US 2005/0143292; US 2005/0153879; US 2005/0158822; US 2005/0158832; US 2005/0170457; US 2005/0181359; US 2005/0181482; US 2005/0192211; US 2005/0202538; US 2005/0227289; US 2005/0244409; US 2006/0088906; US 2006/0111279.

As used herein, the term "analogs", when used with reference to polypeptides, refers to an amino acid sequence that has insertions, deletions or substitutions relative to the parent sequence, while still substantially maintaining the biological activity of the parent sequence, as determined using biological assays known to one of skill in the art. The formulations and methods of the invention may also include "derivatives" of naturally occurring or analog polypeptides which have been chemically modified, for example, to attach water soluble polymers (e.g., pegylated), labels (e.g., radionuclides or various enzymes), or other diagnostic or targeting or therapeutic moieties, or by insertion or substitution of non-natural amino acids by chemical means. Such derivatives will retain the binding properties of underivatized molecules of the invention.

Such polypeptides may be derived from a natural source, constructed by chemical de novo synthesis, or semi-synthesis, or recombinantly expressed, e.g., by expression of an exogenous expression construct, by activation of an endogenous gene (by homologous or non-homologous recombination, for instance), by expression of an exogenous gene under the control of an endogenous transcription control region, or any other techniques known in the art.

Further among exemplary proteins for use in the compositions and methods of the invention are proteins for pharmaceutical formulations that do not induce a highly deleterious antigenic response following administration to a subject. Exemplary in this regard are proteins for veterinary and/or human medical use, particularly, regarding the latter, humanized and human proteins.

Further among exemplary proteins of the invention are proteins that bind selectively to specific targets, including ligand-binding proteins and protein ligands. Antigen-binding proteins, proteins derived therefrom, and proteins related thereto are among the particularly exemplary embodiments of the invention in this regard.

Antibodies

Among particularly exemplary proteins that can be used in the compositions and methods of the present invention are antibody polypeptides. As used herein, the term "antibody" includes heavy or light chains, fully assembled antibodies, heavy, monoclonal antibodies (including human, humanized or chimeric antibodies), polyclonal antibodies, multispecific antibodies (e.g., bispecific antibodies), antibody fragments that can bind antigen (e.g., Fab', F'(ab)2, Fv, single chain antibodies, diabodies), and polypeptides comprising 1, 2, 3, 4, 5 or all 6 complementarity determining regions (CDRs) of the foregoing, and fusion proteins or variants or derivatives thereof, as long as they exhibit the desired binding or biological activity. Antibodies of any isotype class or subclass, including IgG, IgM, IgD, IgA, and IgE, IgG1, IgG2, IgG3, IgG4, IgA1 and IgA2, or any allotype, may be used in the compositions or methods of the present invention. Antibodies may be made by any techniques known in the art, including hybridoma technologies, by activation of an endogenous gene (by homologous or non-homologous recombination, for instance), by expression of an exogenous gene under the control of an endogenous transcription control region, by expression of an exogenous expression construct, by semi-synthesis and by de novo synthesis.

The term "monoclonal antibody" as used herein refers to an antibody obtained from a population of substantially homogeneous antibodies, i.e., the individual antibodies comprising the population are identical except for possible naturally occurring mutations or alternative post-translational modifications that may be present in minor amounts, whether produced from hybridomas or recombinant DNA techniques. Nonlimiting examples of monoclonal antibodies include murine, chimeric, humanized, or human antibodies, or variants or derivatives thereof. Humanizing or modifying antibody sequence to be more human-like is described in, e.g., Jones et al., Nature 321:522 525 (1986); Morrison et al., Proc.

Natl. Acad. Sci., U.S.A., 81:6851 6855 (1984); Morrison and Oi, Adv. Immunol., 44:65 92 (1988); Verhoeyer et al., Science 239:1534 1536 (1988); Padlan, Molec. Immun. 28:489 498 (1991); Padlan, Molec. Immunol. 31(3):169 217 (1994); and Kettleborough, C. A. et al., Protein Eng. 4(7):773 83 (1991); Co, M. S., et al. (1994), J. Immunol. 152, 2968-2976); Studnicka et al. Protein Engineering 7: 805-814 (1994); each of which is incorporated herein by reference. One method for isolating human monoclonal antibodies is the use of phage display technology. Phage display is described in e.g., Dower et al., WO 91/17271, McCafferty et al., WO 92/01047, and Caton and Koprowski, Proc. Natl. Acad. Sci. USA, 87:6450-6454 (1990), each of which is incorporated herein by reference. Another method for isolating human monoclonal antibodies uses transgenic animals that have no endogenous immunoglobulin production and are engineered to contain human immunoglobulin loci. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993); WO 91/10741, WO 96/34096, WO 98/24893, or U.S. patent application publication nos. 20030194404, 20030031667 or 20020199213; each incorporated herein by reference.

Antibody fragments may be produced by recombinant DNA techniques or by enzymatic or chemical cleavage of intact antibodies. "Antibody fragments" comprise a portion of an intact full length antibody, preferably the antigen binding or variable region of the intact antibody, and include multispecific (bispecific, trispecific, etc.) antibodies formed from antibody fragments. Nonlimiting examples of antibody fragments include Fab, Fab', F(ab')$_2$, Fv (variable region), domain antibodies (dAb, containing a VH domain; Ward et al., Nature 341:544-546, 1989), complementarity determining region (CDR) fragments, single-chain antibodies (scFv, containing VH and VL domains on a single polypeptide chain; Bird et al., Science 242:423-426, 1988, and Huston et al., Proc. Natl. Acad. Sci. USA 85:5879-5883, 1988, optionally including a polypeptide linker; and optionally multispecific, Gruber et al., J. Immunol. 152: 5368 (1994)), single chain antibody fragments, diabodies (VH and VL domains on a single polypeptide chain that pair with complementary VL and VH domains of another chain; EP 404,097; WO 93/11161; and Hollinger et al., Proc. Natl. Acad. Sci. USA, 90:6444-6448 (1993)), triabodies, tetrabodies, minibodies (scFv fused to CH3 via a peptide linker (hingeless) or via an IgG hinge; Olafsen, et al., Protein Eng Des Sel. 2004 April; 17(4):315-23), linear antibodies (tandem Fd segments (VH-CH1-VH-CH1; Zapata et al., Protein Eng., 8(10):1057-1062 (1995)); chelating recombinant antibodies (crAb, which can bind to two adjacent epitopes on the same antigen; Neri et al., J Mol. Biol. 246:367-73, 1995), bibodies (bispecific Fab-scFv) or tribodies (trispecific Fab-(scFv)(2); Schoonjans et al., J. Immunol. 165:7050-57, 2000; Willems et al., J Chromatogr B Analyt Technol Biomed Life Sci. 786:161-76, 2003), intrabodies (Biocca, et al., EMBO J. 9:101-108, 1990; Colby et al., Proc Natl Acad Sci USA. 101:17616-21, 2004) which may also comprise cell signal sequences which retain the antibody intracellularly (Mhashilkar et al, EMBO J. 14:1542-51, 1995; Wheeler et al., FASEB J. 17:1733-5, 2003), transbodies (cell-permeable antibodies containing a protein transduction domain (PTD) fused to scFv; Heng et al., Med. Hypotheses. 64:1105-8, 2005) nanobodies (approximately 15 kDa variable domain of the heavy chain; Cortez-Retamozo et al., Cancer Research 64:2853-57, 2004, small modular immunopharmaceuticals (SMIPs; WO 03/041600, U.S. Patent publication 2003/0133939 and US Patent Publication 2003/0118592), an antigen-binding-domain immunoglobulin fusion protein, a camelized antibody (in which VH recombines with a constant region that contains hinge, CH1, CH2 and CH3 domains; Desmyter et al., J. Biol. Chem. 276:26285-90, 2001; Ewert et al., Biochemistry 41:3628-36, 2002; U.S. Patent Publication Nos. 20050136049 and 20050037421), a VHH containing antibody, heavy chain antibodies (HCAbs, homodimers of two heavy chains having the structure H2L2), or variants or derivatives thereof, and polypeptides that contain at least a portion of an immunoglobulin that is sufficient to confer specific antigen binding to the polypeptide, such as a CDR sequence, as long as the antibody retains the desired biological activity.

The term "hypervariable" region or "complementarity determining region" (CDR) refers to residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991); or an alternative definition of CDR residues from a hypervariable "loop" is described by Chothia et al., J. Mol. Biol. 196: 901-917 (1987) as residues 26-32 (L1), 50-52 (L2) and 91-96 (L3) in the light chain variable domain and 26-32 (H1), 53-55 (H2) and 96-101 (H3) in the heavy chain variable domain). "Framework" residues are those variable region residues other than the hypervariable region residues.

The term "variant" when used in connection with antibodies refers to polypeptide sequence of an antibody that contains at least one amino acid substitution, deletion, or insertion in the variable region or the portion equivalent to the variable region, provided that the variant retains the desired binding affinity or biological activity. In addition, the antibodies of the invention may have amino acid modifications in the constant region to modify effector function of the antibody, including half-life or clearance, ADCC and/or CDC activity. Such modifications can enhance pharmacokinetics or enhance the effectiveness of the antibody in treating cancer, for example. See Shields et al., J. Biol. Chem., 276(9): 6591-6604 (2001), incorporated by reference herein in its entirety.

The term "derivative" when used in connection with antibodies refers to antibodies covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. Derivatives of the invention will retain the binding properties of underivatized molecules of the invention. Conjugation of cancer-targeting antibodies to cytotoxic agent, for example, radioactive isotopes (e.g., I131, I125, Y90 and Re186), chemotherapeutic agents, or toxins, may enhance destruction of cancerous cells.

Methods for making bispecific or other multispecific antibodies are known in the art and include chemical cross-linking, use of leucine zippers (Kostelny et al., J. Immunol. 148:1547-1553, 1992)]; diabody technology (Hollinger et al., Proc. Natl. Acad. Sci. USA 90:6444-48, 1993); scFv dimers (Gruber et al., J. Immunol. 152: 5368, 1994), linear antibodies (Zapata et al., Protein Eng. 8:1057-62, 1995); and chelating recombinant antibodies (Neri et al., J Mol. Biol. 246:367-73, 1995).

Target Binding Proteins

Also among exemplary proteins of the invention in this regard are other types of target binding proteins, and proteins relating thereto or derived therefrom, and protein ligands, and proteins derived therefrom or relating thereto, particularly those comprising an Fc region of an antibody or a variant or derivative of an Fc region. Among exemplary ligand-binding proteins in this regard are proteins that bind signal and effector proteins, and proteins relating thereto or derived therefrom.

Peptibodies, molecules comprising an antibody Fc domain attached to at least one antigen-binding peptide, are generally described in PCT publication WO 00/24782, published May 4, 2000. Immunoglobulin-like proteins, members of the immunoglobulin superfamily, contain one or more immunoglobulin-like domains which fold in structures similar to portions of the antibody variable region.

Also contemplated with respect to the compositions and methods of the invention are formulations containing protein scaffolds that may comprise a single protein chain or a multi-polypeptide complex. Exemplary protein scaffolds are avimers, which are avidity multimers that contain a single protein chain made up of multiple domains, each of which represents a separate function (Silverman et al., Nat Biotech 23(12): 1556-1561 (2005); U.S. Patent Publication No. US 2005/0089932 A1; each of which is incorporated by reference herein in its entirety). Other protein scaffolds are reviewed in Razeghifard et al., Current Protein & Peptide Science. 8(1): 3-18, 2007, incorporated by reference herein in its entirety. Other protein scaffolds suitable for displaying peptides are reviewed in Hosse et al., Protein Science 15:14-27, 2006 (reviewing scaffolds such as the fibronectin type III domain, a lipocalin, a knottin, cytochrome b562, a kunitz-type protease inhibitor, the Z-domain, and the carbohydrate binding module CBM4-2), incorporated by reference herein in its entirety. See also Gill et al., Current Opin. Biotechnol., 17:653-658 (2006) (single domain antibodies, small modular immunopharmaceuticals, tetranectins, Adnectins, A-domain proteins, lipocalins, ankylin repeat proteins), and Skerra, J. Mol. Recognit., 13:167-187 (2000) (single domains of antibodies or of immunoglobulin superfamily, protease inhibitors, helix bundle proteins, disulfide-knotted peptides, and lipocalins), each of which is incorporated by reference herein in its entirety.

Target binding proteins, including antibodies, peptibodies, Fc fusion proteins, avimers and other protein scaffolds, and analogs or variants or derivatives thereof, that can be used in the compositions and methods of the present invention include those that bind to one or more of the following, alone or in any combination:

(i) CD proteins including but not limited to CD3, CD4, CD8, CD19, CD20, CD22, CD30, and CD34; including those that interfere with receptor binding.

(ii) HER receptor family proteins, including, for instance, HER2, HER3, HER4, and the EGF receptor;

(iii) cell adhesion molecules, for example, LFA-1, Mol, p150,95, VLA-4, ICAM-1, VCAM, and alpha v/beta 3 integrin;

(iv) growth factors, including but not limited to, for example, vascular endothelial growth factor ("VEGF"), growth hormone, thyroid stimulating hormone, follicle stimulating hormone, luteinizing hormone, growth hormone releasing factor, parathyroid hormone, mullerian-inhibiting substance, human macrophage inflammatory protein (MIP-1-alpha), erythropoietin (EPO), nerve growth factor, such as NGF-beta, platelet-derived growth factor (PDGF), fibroblast growth factors, including, for instance, aFGF and bFGF, epidermal growth factor (EGF), transforming growth factors (TGF), including, among others, TGF-alpha and TGF-beta, including TGF-beta1, TGF-beta2, TGF-beta3, TGF-beta4, or TGF-beta5, insulin-like growth factors-I and -II (IGF-I and IGF-II), des(1-3)-IGF-I (brain IGF-I), and osteoinductive factors;

(v) insulins and insulin-related proteins, including but not limited to insulin, insulin A-chain, insulin B-chain, proinsulin, and insulin-like growth factor binding proteins;

(vi) coagulation and coagulation-related proteins, such as, among others, factor VIII, tissue factor, von Willebrands factor, protein C, alpha-1-antitrypsin, plasminogen activators, such as urokinase and tissue plasminogen activator ("t-PA"), bombazine, thrombin, and thrombopoietin;

(vii) other blood and serum proteins, including but not limited to albumin, IgE, and blood group antigens;

(viii) colony stimulating factors (CSFs) and receptors thereof, including the following, among others, M-CSF, GM-CSF, and G-CSF, and receptors thereof, such as CSF-1 receptor (c-fms);

(ix) receptors and receptor-associated proteins, including, for example, flk2/flt3 receptor, obesity (OB) receptor, growth hormone receptors, thrombopoietin receptors ("TPO -R," "c-mpl"), glucagon receptors, interleukin receptors, interferon receptors, T-cell receptors, stem cell factor receptors (scfr's), such as c-Kit, and other receptors listed herein;

(x) receptor ligands, including, for example, OX40L, the ligand for the OX40 receptor expressed on T cells, and other ligands listed herein;

(xi) neurotrophic factors, including but not limited to, bone-derived neurotrophic factor (BDNF) and neurotrophin-3, -4, -5, or -6 (NT-3, NT-4, NT-5, or NT-6);

(xii) relaxin A-chain, relaxin B-chain, and prorelaxin;

(xiii) interferons and interferon receptors, including for example, interferon-alpha, -beta, and -gamma, and interferon-alpha, -beta, and -gamma receptors;

(xiv) interleukins (ILs) and interleukin receptors, including but not limited to IL-1 to IL-15 and IL-1 to IL-15 receptors, such as the IL-8 receptor, among others;

(xv) viral antigens, including but not limited to, an AIDS envelope viral antigen;

(xvi) lipoproteins, calcitonin, glucagon, atrial natriuretic factor, lung surfactant, tumor necrosis factor-alpha and -beta, enkephalinase, RANTES (regulated on activation normally T-cell expressed and secreted), mouse gonadotropin-associated peptide, DNAse, inhibin, and activin;

(xvii) integrin, protein A or D, rheumatoid factors, immunotoxins, bone morphogenetic protein (BMP), superoxide dismutase, surface membrane proteins, decay accelerating factor (DAF), AIDS envelope, transport proteins, homing receptors, addressins, regulatory proteins, immunoadhesins, antibodies;

(xviii) myostatins, TALL proteins, including TALL-1, amyloid proteins, including but not limited to amyloid-beta proteins, thymic stromal lymphopoietins ("TSLP"), RANK ligand ("OPGL"), c-kit, TNF receptors, including TNF Receptor Type 1, TRAIL-R2, angiopoietins, and (xix) biologically active fragments or analogs or variants of any of the foregoing.

As to all of the foregoing, particularly exemplary are those that are effective therapeutic agents, particularly those that exert a therapeutic effect by binding a target, particularly a target among those listed above, including targets derived therefrom, targets related thereto, and modifications thereof.

Particular Illustrative Proteins

Exemplary therapeutic polypeptides suitable for use in the formulations and methods of the invention include human erythropoietin (SEQ ID NO: 1) or biologically active variants, derivatives, or analogs thereof, including chemically modified derivatives. One exemplary protein is darbepoetin (SEQ ID NO: 2). Darbepoetin is a hyperglycosylated erythropoietin analog having five changes in the amino acid sequence of recombinant human EPO which provide for two additional N-linked carbohydrate chains at amino acid residues 30 and 88.

Figure 2:
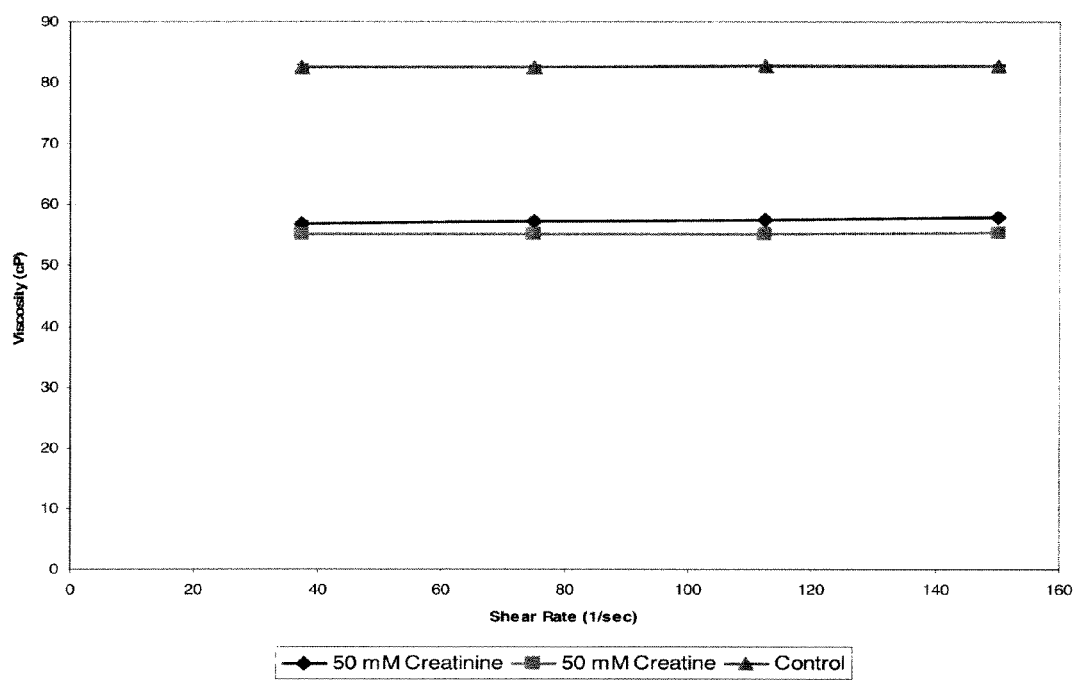
FIG. 2. The effect of 50 mM creatine and 50 mM creatinine on Antibody A viscosity. Creatine and creatinine both cause a significant decrease in the viscosity of a formulation containing 235 mg/ml Antibody A in 10 mM sodium acetate pH 5.20. At equilibrium, the decrease in formulation viscosity is constant whether starting with 50 mM creatine or 50 mM creatinine.
Figure 4:
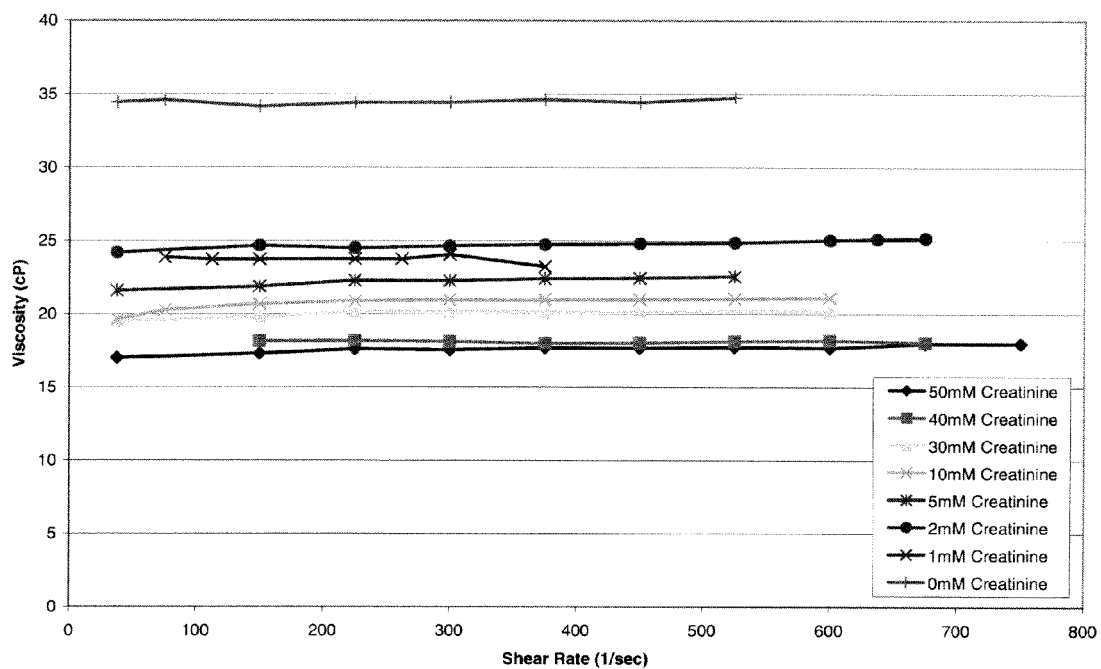
FIG. 4. Effect of varying creatinine/creatine concentrations on viscosity of a formulation containing 200 mg/ml Antibody A.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in International Publication Number WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication.

Myostatin binding proteins, peptibodies, and related proteins, and the like, including myostatin specific peptibodies, particularly those described in US Application Publication Number 2004/0181033 and International Publication Number WO 2004/058988 which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication.

IL-4 receptor specific antibodies, peptibodies, and related proteins, and the like, particularly those that inhibit activities mediated by binding of IL-4 and/or IL-13 to the receptor, including those described in International Publication No. WO 2005/047331 of International Application Number PCT/US2004/03742 and in US patent application publication number 2005/112694, which are incorporated herein by reference in there entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication.

Interleukin 1-receptor 1 ("IL1-R1") specific antibodies, peptibodies, and related proteins, and the like, including but not limited to those described in U.S. Application Publication Number US2004/097712A1 which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. application publication.

Ang2 specific antibodies, peptibodies, and related proteins, and the like, including but not limited to those described in International Publication Number WO 03/057134 and U.S. Application Publication Number US2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C$_1$K; 2×L1C; Con4C; Con4C$_1$K; 2×Con4C$_1$K; Con4-L1 (N); Con4-L1C; TN-12-9 (N); C17 (N); TN8-8(N); TN8-14 (N); Con 1 (N), also including anti-Ang 2 antibodies and formulations such as those described in International Publication Number WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication.

NGF specific antibodies, peptibodies, and related proteins, and the like including, in particular, but not limited to those described in US Application Publication Number US2005/0074821 and U.S. Pat. No. 6,919,426 which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication.

CD22 specific antibodies, peptibodies, and related proteins, and the like, such as those described in U.S. Pat. No. 5,789,554 which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0.

IGF-1 receptor specific antibodies, peptibodies, and related proteins, and the like, such as those described in International Patent Application Number PCT/US2005/046493, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50HS0, L51H51, L52H52, and IGF-1R-binding fragments and derivatives thereof, each of which is individually and specifically incorporated by reference herein in its entirety fully as disclosed in the foregoing International Application.

Also among non-limiting examples of anti-IGF-1R antibodies for use in the methods and compositions of the present invention are each and all of those described in:

US Pat. App. Pub. No. 06/0040358 (published Feb. 23, 2006), 05/0008642 (published Jan. 13, 2005), 04/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

PCT Pub. No. WO 06/138729 (published Dec. 28, 2006), WO 05/016970 (published Feb. 24, 2005), and Lu et al., 2004, J Biol. Chem. 279:2856-65, including but not limited to antibodies 2F8, A12, and IMC-A12 as described therein;

PCT Pub. No. WO 07/012,614 (published Feb. 1, 2007), WO 07/000,328 (published Jan. 4, 2007), WO 06/013472 (published Feb. 9, 2006), and 05/058967 (published Jun. 30, 2005), 03/059951 (published Jul. 24, 2003);

US Pat. App. Pub. No. 05/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

US Pat. App. Pub. No. 05/0249728 (published Nov. 10, 2005), 05/0186203 (published Aug. 25, 2005), 04/0265307 (published Dec. 30, 2004), 03/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

U.S. Pat. No. 7,037,498 (issued May 2, 2006), US Pat. App. No. 05/0244408 (published Nov. 30, 2005), 04/0086503 (published May 6, 2004), Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

US Pat. App. No. 05/0136063 (published Jun. 23, 2005), 04/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein;

US Pat. App. No. 04/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors.

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Provisional Application No. 60/700,265, filed 18 Jul. 2005 and International Publication Number WO07/011,941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Provisional Application.

IL-15 specific antibodies, peptibodies, and related proteins, and the like, such as, in particular, humanized monoclonal antibodies, particularly antibodies such as those disclosed in U.S. Application Publication Numbers: US2003/0138421; US2003/023586; US2004/0071702; and U.S. Pat. No. 7,153,507 each of which is incorporated herein by reference in its entirety as to IL-15 specific antibodies and related proteins, including peptibodies, including particularly, for instance, but not limited to, HuMax IL-15 antibodies and related proteins, such as, for instance, 146B7.

IFN gamma specific antibodies, peptibodies, and related proteins and the like, especially human IFN gamma specific antibodies, particularly fully human anti-IFN gamma antibodies, such as, for instance, those described in US Application Publication Number US 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Application Publication US 2005/0004353 and in Thakur et al., *Mol. Immunol.* 36:1107-1115 (1999). In addition, description of the properties of these antibodies provided in US Patent Application No. US 2005/0004353 is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in US Patent Publication No. 2005/0004353. A specific antibody contemplated is antibody 1119 as disclosed in US Patent Pub No. 2005/0004353 and having a complete heavy chain of SEQ ID NO:17 as disclosed therein and having a complete light chain of SEQ ID NO:18 as disclosed therein.

TALL-1 specific antibodies, peptibodies, and the related proteins, and the like, and other TALL specific binding proteins, such as those described in U.S. Application Publication Numbers 2003/0195156 and 2006/135431 each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Application Publication.

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH.

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R.

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Patent Application Publication Number US2005/0118643 and International Publication Number WO2005/017107, huL2G7 described in U.S. Pat. No. 7,220,410 and OA-5d5 described in U.S. Pat. Nos. 5,686,292, 6,468,529, and in International Publication Number WO 96/38557, each of which is incorporated herein by reference in its entirety, particularly in parts pertinent to proteins that bind HGF.

TRAIL-R2 specific antibodies, peptibodies, related proteins and the like, such as those described in U.S. Provisional Applications 60/713,433 filed 31 Aug. 2005 and 60/713,478 filed 31 Aug. 2005, each of which is herein incorporated by reference in its entirety, particularly in parts pertinent to proteins that bind TRAIL-R2.

Activin A specific antibodies, peptibodies, related proteins, and the like, including but not limited to those described in U.S. Provisional Patent Application No. 60/843,430 filed 8 Sep. 2006, which is herein incorporated by reference in its entirety, particularly in parts pertinent to proteins that bind Activin A.

TGF-beta specific antibodies, peptibodies, related proteins, and the like, including but not limited to those described in U.S. Pat. No. 6,803,453 and US Patent Application Publication Number 2007/110747, each of which is herein incorporated by reference in its entirety, particularly in parts pertinent to proteins that bind TGF-beta.

Amyloid-beta protein specific antibodies, peptibodies, related proteins, and the like, including but not limited to those described in International Publication Number WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in WO 2006/081171.

c-Kit specific antibodies, peptibodies, related proteins, and the like, including but not limited to those described in U.S. Provisional Patent Application No. 60/794,771, which is incorporated herein by reference in its entirety, particularly in parts pertinent to proteins that bind c-Kit and/or other stem cell factor receptors.

OX40L specific antibodies, peptibodies, related proteins, and the like, including but not limited to those described in U.S. patent application Ser. No. 11/086,289, which is incorporated herein by reference in its entirety, particularly in parts pertinent to proteins that bind OX40L and/or other ligands of the OX40 receptor.

Other exemplary proteins include Activase® (Alteplase, tPA); Aranesp® (Darbepoetin-alfa), Epogen® (Epoetin alfa, or erythropoietin); Avonex® (Interferon beta-1a); Bexxar® (Tositumomab, anti-CD22 monoclonal antibody); Betaseron® (Interferon-beta); Campath® (Alemtuzumab, anti-CD52 monoclonal antibody); Dynepo® (Epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (Epoetin alfa); Erbitux® (Cetuximab, anti-EGFR/ HER1/c-ErbB-1); Genotropin® (Somatropin, Human Growth Hormone); Herceptin® (Trastuzumab, anti-HER2/ neu (erbB2) receptor mAb); Humatrope® (Somatropin, Human Growth Hormone); Humira® (Adalimumab); Insulin in Solution; Infergen® (Interferon Alfacon-1); Natrecor® (nesiritide; recombinant human B-type natriuretic peptide (hBNP); Kineret® (Anakinra), Leukine® (Sargamostim, rhuGM-CSF); LymphoCide® (Epratuzumab, anti-CD22 mAb); Lymphostat B® (Belimumab, anti-BlyS mAb); Metalyse® (Tenecteplase, t-PA analog); Mircera® (methoxy polyethylene glycol-epoetin beta); Mylotarg® (Gemtuzumab ozogamicin); Raptiva® (efalizumab); Cimzia® (certolizumab pegol, CDP 870); Soliris™ (Eculizumab); Pexelizumab (Anti-05 Complement); MEDI-524 (Numax®); Lucentis® (Ranibizumab); 17-1A (Edrecolomab, Panorex®); Trabio® (lerdelimumab); TheraCim hR3 (Nimotuzumab); Omnitarg (Pertuzumab, 2C4); Osidem® (IDM-1); OvaRex® (B43.13); Nuvion® (visilizumab); Cantuzumab mertansine (huC242-DM1); NeoRecormon® (Epoetin beta); Neumega® (Oprelvekin, Human Interleukin-11); Neulasta® (Pegylated filgastrim, pegylated G-CSF, pegylated hu-Met-G-CSF); Neupogen® (Filgrastim™, G-CSF, hu-MetG-CSF); Orthoclone OKT3® (Muromonab-CD3, anti-CD3 monoclonal antibody), Procrit® (Epoetin alfa); Remicade® (Infliximab, anti-TNFα monoclonal antibody), Reopro® (Abciximab, anti-GP IIb/IIIa receptor monoclonal antibody), Actemra® (anti-IL6 Receptor mAb), Avastin® (Bevacizumab), HuMax-CD4 (zanolimumab), Rituxan® (Rituximab, anti-CD20 mAb); Tarceva® (Erlotinib); Roferon-A®- (Interferon alfa-2a); Simulect® (Basiliximab); Prexige® (lumiracoxib); Synagis® (Palivizumab); 146B7-CHO (anti-IL15 antibody, see U.S. Pat. No. 7,153,507), Tysabri® (Natalizumab, anti-α4integrin mAb); Valortim® (MDX-1303, anti-B. anthracis Protective Antigen mAb); ABthrax™; Vectibix® (Panitumumab); Xolair® (Omalizumab), ETI211 (anti-MRSA mAb), IL-1 Trap (the Fc portion of human IgG1 and the extracellular domains of both IL-1 receptor components (the Type I receptor and receptor accessory protein)), VEGF Trap (Ig domains of VEGFR1 fused to IgG1 Fc), Zenapax® (Daclizumab); Zenapax® (Daclizumab, anti-IL-2Rα mAb), Zevalin® (Ibritumomab tiuxetan), Zetia (ezetimibe), Atacicept (TACI-Ig), anti-CD80 monoclonal antibody (mAb) (galiximab), anti-CD23 mAb (lumiliximab).

BR2-Fc (huBR3/huFc fusion protein, soluble BAFF antagonist); CNTO 148 (Golimumab, anti-TNFα mAb); HGS-ETR1 (Mapatumumab; human anti-TRAIL Receptor-1 mAb); HuMax-CD20 (Ocrelizumab, anti-CD20 human mAb); HuMax-EGFR (zalutumumab); M200 (Volociximab, anti-α5β1 integrin mAb); MDX-010 (Ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); Adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1 mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/F1t-1 mAb; anti-ZP3 mAb (HuMax-ZP3); NVS Antibody #1; and NVS Antibody #2.

Sequence Variation

Particularly exemplary proteins in regard to all of the foregoing and the following, include those that comprise a region that is 70% or more, 80% or more, 90% or more, 95% or more, 97% or more, 98% or more, or 99% or more identical in amino acid sequence to a reference amino acid sequence of a binding protein, as illustrated above, particularly a pharmaceutical binding protein, such as a GenBank or other reference sequence of a reference protein.

Identity in this regard can be determined using a variety of well-known and readily available amino acid sequence analysis software. Exemplary software includes those that implement the Smith-Waterman algorithms, considered a satisfactory solution to the problem of searching and aligning sequences. Other algorithms also may be employed, particularly where speed is an important consideration. Commonly employed programs for alignment and homology matching of DNAs, RNAs, and polypeptides that can be used in this regard include FASTA, TFASTA, BLASTN, BLASTP, BLASTX, TBLASTN, PROSRCH, BLAZE, and MPSRCH, the latter being an implementation of the Smith-Waterman algorithm for execution on massively parallel processors made by Mas-Par.

The BLASTN, BLASTX, and BLASTP programs are among exemplary programs for such determinations, the former for polynucleotide sequence comparisons and the latter two for polypeptide sequence comparisons; particularly BLASTX for comparison of the polypeptide sequences from all three reading frames of polynucleotide sequence and BLASTP for a single polypeptide sequence.

BLAST provides a variety of user definable parameters that are set before implementing a comparison. Some of them are more readily apparent than others on graphical user interfaces, such as those provided by NCBI BLAST and other sequence alignment programs that can be accessed on the internet. The settings and their values are set out and explained on the service web sites and are explained and set out in particular detail in a variety of readily available texts, including but not limited to BIOINFORMATICS: SEQUENCE AND GENOME ANALYSIS, 2nd Ed., David W. Mount, Cold Spring Harbor Laboratory Press, Cold Spring Harbor, N.Y. (2004), especially Chapters 3, 4, 5, and 6 as to comparison of protein and nucleic acid sequences in general and as to BLAST comparisons and searches in particular; SEQUENCE ANALYSIS IN A NUTSHELL: A GUIDE TO COMMON TOOLS AND DATABASES, Scott Markel and Darryl León, O'Reilly & Associates, Sebastopol, Calif. (2003), especially Chapter 7 as to BLAST in particular, each of which is herein incorporated by reference in its entirety particularly in parts pertinent to comparison of nucleotide and polypeptide sequences and to determining their degree of identity, similarity, homology and/or the like, especially as to comparison of a test sequence and a reference sequence to calculate a degree (percent) of identity between them.

In exemplary embodiments of the invention in this regard, relatedness of sequences is defined as the identity score in percent returned by any one or another of the aforementioned BLAST comparison searches with e=10 and all other parameters set to their default values on the NCBI web server as set forth in SEQUENCE ANALYSIS IN A NUTSHELL: A GUIDE TO COMMON TOOLS AND DATABASES, Scott Markel and Darryl Leon, O'Reilly & Associates, Sebastopol, Calif. (2003), pages 47-51 which are incorporated herein by reference in their entireties and in all particulars of the exemplary settings for parameters of the present invention for comparing sequences using BLAST, such as those on NCBI BLAST.

The following references provide additional information on sequence comparisons in this regard, and in others. GUIDE TO HUMAN GENOME COMPUTING, Ed. Martin J. Bishop, Academic Press, Harcourt Brace & Company Publishers, New York (1994), which is incorporated herein by reference in its entirety with regard to the foregoing, particularly in parts pertinent to determining identity and or homology of amino acid or polynucleotide sequences, especially Chapter 7. The BLAST programs are described in Altschul et al., "Basic Local Alignment Research Tool," J Mol Biol 215: 403-410 (1990), which is incorporated by reference herein in its entirety. Additional information concerning sequence analysis and homology and identity determinations are provided in, among many other references well-known and readily available to those skilled in the art: NUCLEIC ACID AND PROTEIN SEQUENCE ANALYSIS: A PRACTICAL APPROACH, Eds. M. J. Bishop and C. J. Rawings, IRL Press, Oxford, UK (1987); PROTEIN STRUCTURE: A PRACTICAL APPROACH, Ed. T. E. Creighton, IRL Press, Oxford, UK (1989); Doolittle, R. F.: "Searching through sequence databases," Met Enz. 183: 99-110 (1990); Meyers and Miller: "Optimal alignments in linear space" Comput. Applica. in Biosci 4: 11-17 (1988); Needleman and Wunsch: "A general method applicable to the search for similarities in amino acid sequence of two proteins," J Mol Biol 48: 443-453 (1970) and Smith and Waterman "Identification of common molecular subsequences," J Mol Biol 147: 1950 et seq. (1981), each of which is incorporated herein by reference in its entirety with reference to the foregoing, particularly in parts pertinent to sequence comparison and identity and homology determinations.

II. Preparation of Formulations of the Invention

Stable pharmaceutical formulations of therapeutic protein with minimal degradation, precipitation and/or aggregation are commercially desirable. In particular, when large doses of therapeutic protein are to be administered in a small volume of liquid, it is highly desirable to provide formulations with high concentrations of protein that do not exhibit the increased viscosity typically seen with such high protein concentrations. High viscosity formulations are difficult to handle during manufacturing, including at the bulk and filling stages. In addition, high viscosity formulations are difficult to draw into a syringe and inject, often necessitating use of lower gauge needles. Protein solutions also have the potential for particulate formulation and aggregation, which may impact activity, effectiveness and possibly immunogenicity of the therapeutic protein. As shown herein, the addition of creatinine/creatine or carnitine to solutions of biologically active protein unexpectedly reduces the viscosity of the protein solutions and also reduces the protein aggregation observed under conditions of thermal stress.

The use of an excipient selected from the group consisting of creatinine, creatine, carnitine, or mixtures thereof, permits a higher concentration of therapeutic proteins to be used in the formulation without a concomitant increase in viscosity and/or aggregation. The improved stability from the reduced aggregation results in a formulation with an increased shelf life, particularly at refrigerator temperature but also at higher temperatures as well, e.g., room temperature.

Thus, the invention provides a method for stabilizing or reducing viscosity of protein formulations by adding an excipient selected from the group consisting of creatinine, creatine, carnitine, or mixtures thereof, in an amount effective to stabilize and/or reduce viscosity. The invention also provides stable or reduced-viscosity formulations of therapeutic protein, including antibody, containing effective amounts or concentrations of an excipient selected from the group consisting of creatinine, creatine, carnitine, or mixtures thereof. Also contemplated are methods of screening one or more formulations, each containing different concentrations of creatinine, creatine, carnitine, or mixtures thereof, to identify suitable or optimal concentrations that reduce viscosity and/or aggregation. Further provided are methods of preparing a lyophilized powder from reduced-viscosity solution formulations of the invention, and methods of reconstituting the lyophilized powders of the invention via addition of a sterile diluent.

Thus, the present invention provides pharmaceutical formulations containing biologically active polypeptides and viscosity-reducing concentrations of excipients. The reduction in viscosity is at least about 10-70% versus non-excipient controls. In one embodiment the reduction in viscosity ranges from about 10-30%. In other exemplary embodiments, the reduction in viscosity is at least 5%, 10%, 15%, 20%, 25%, 30%, 35%, 40%, 45%, 50%, 55%, 60%, or 65%.

Stable formulations according to the present invention may exhibit a longer shelf life at 2-8° C. (refrigerator temperature), for example, at least 1 month, 2 months, 3 months, 6 months, 9 months, 1 year, 18 months or 2 years, and also results in a longer shelf life at other temperatures, such as 25-30° C. (room temperature).

Formulations of the invention may optionally include pharmaceutically acceptable salts, buffers, surfactants, excipients, carriers, diluents, and/or other formulation agents.

Exemplary pharmaceutically acceptable buffers include acetate (e.g. sodium acetate), succinate (such as sodium succinate), gluconate, histidine, citrate or other organic acid buffers. Exemplary buffer concentration can be from about 1 mM to about 200 mM, or from about 10 mM to about 60 mM, depending, for example, on the buffer and the desired tonicity (e.g. isotonic, hypertonic or hypotonic) of the formulation. Exemplary pHs include from about 4.5 to about 6.5, or from about 4.8 to about 5.5, or from about 4 to 6, or about 5 to 5.5, or about 5, greater than about 5, greater than about 5.5, greater than about 6, or greater than about 6.5.

Suitable diluents, excipients, or carriers and other agents include, but are not limited to, antioxidants, coloring, flavoring and diluting agents, emulsifying agents, suspending agents, solvents, fillers, bulking agents, buffers, vehicles, diluents, excipients and/or pharmaceutical adjuvants. For example, a suitable vehicle may be, physiological saline solution, citrate buffered saline, or artificial CSF, possibly supplemented with other materials common in compositions for parenteral administration. Neutral buffered saline or saline mixed with serum albumin are further exemplary vehicles. Those skilled in the art would readily recognize a variety of buffers that could be used in the compositions, and dosage forms used in the invention. Typical buffers include, but are not limited to pharmaceutically acceptable weak acids, weak bases, or mixtures thereof. Exemplary buffer components are water soluble materials such as phosphoric acid, tartaric acids, lactic acid, succinic acid, citric acid, acetic acid, ascorbic acid, aspartic acid, glutamic acid, or salts thereof. Exemplary salts include inorganic and organic acids, or bases such as metals or amines, in exemplary concentrations such as about 50-200 mM, or 100-200 mM, or about 100 mM, or about 150 mM.

Other excipients or stabilizers may also be included, for example, sugars (e.g., sucrose, glucose, trehalose, fructose, xylose, mannitose, fucose), polyols (e.g., glycerol, mannitol, sorbitol, glycol, inositol), amino acids or amino acid derivatives (e.g., glycine, glycine betaine, proline, valine, leucine, alanine, glutamine, taurine), or surfactants (e.g., polysorbate, including polysorbate 20, or polysorbate 80, or poloxamer, including poloxamer 188). Exemplary concentrations of surfactant may range from about 0.001% to about 0.5%, or from about 0.005% to about 0.2%. Preservatives may also be included, such as benzyl alcohol, phenol, m-cresol, chlorobutanol or benzethonium Cl, e.g. at concentrations ranging from about 0.1% to about 2%, or from about 0.5% to about 1%.

One or more other pharmaceutically acceptable carriers, excipients or stabilizers such as those described in Remington's Pharmaceutical Sciences 16th edition, Osol, A. Ed. (1980) may be included in the formulation provided that they do not adversely affect the desired characteristics of the formulation.

The concentration of therapeutic protein, such as antibody, in the formulation will depend upon the end use of the pharmaceutical formulation and can be easily determined by a person of skill in the art. Therapeutic proteins that are antagonists are frequently administered at higher concentrations than those that are agonists. Particularly contemplated high concentrations of therapeutic proteins (without taking into account the weight of chemical modifications such as pegylation), including antibodies, are at least about 70, 80, 90, 100, 110, 120, 130, 140, 150, 175, 200, 250, 300, 350, 400, 450, or 500 mg/ml, and/or less than about 250, 300, 350, 400, 450 or 500 mg/ml. Exemplary high concentrations of therapeutic protein, such as antibody, in the formulation may range from at least about 100 mg/ml to about 500 mg/ml. Other protein concentrations (without taking into account the weight of chemical modifications such as pegylation), are also contemplated, e.g., at least about 1, 5, 10, 20, 30, 35, 40, 45, 50, 55, 60, 65 or 70 mg/ml. The invention particularly contemplates formulations and methods in which the concentration of therapeutic protein results in a viscosity of at least 6, 8, 10, 12, 14, 16, 18, 20, 25, 30 cP or higher and the inclusion of creatine, creatinine, carnitine, or a combination thereof results in the reduction of the viscosity by 5% or greater. For example, a solution with a viscosity of about 20 cP may be difficult to inject with a standard 27 gauge needle. With respect to antibodies or proteins of a molecular weight of about 150 kD or higher, concentrations of about 70 mg/ml or higher may be associated with such increased viscosity. With respect to smaller proteins, e.g. of a molecular weight of about 75 kD or less, e.g. 50 kD or less, concentrations of about 30 mg/ml or higher may be associated with such increased viscosity. Chemical modification of such smaller proteins may cause the viscosity of solutions containing the modified protein to increase relative to the non-modified protein. All references to mg/ml concentration of therapeutic protein, weight of therapeutic protein (mg) or molecular weight of therapeutic protein (kD) herein mean the respective weight of the proteinaceous part of the therapeutic protein, excluding any non-proteinaceous modifications.

The present invention provides a method of reducing the viscosity of and/or improving stability of a liquid pharmaceutical formulation of a therapeutic protein, by combining the therapeutic protein and a viscosity-reducing amount or aggregation-reducing amount of an excipient selected from the group consisting of creatinine, creatine or carnitine, or mixtures thereof. In exemplary embodiments, the therapeutic protein is at a high protein concentration as described above. In some embodiments, the reduction in viscosity is at least about 5%, 10%, 15%, 20%, 25%, 30%, 35%, 40%, 45%, 50%, 55%, 60%, 65% or 70% compared to excipient-free controls. In other embodiments, the reduction in aggregation induced by thermal stress is at least about 5%, 10%, 15%, 20%, 25%, 30%, 35%, 40%, 45%, 50%, 55%, 60%, 65% or 70% compared to excipient-free controls.

In another aspect, the invention provides liquid solutions comprising a therapeutic protein and an excipient selected from the group consisting of creatinine, creatine or carnitine, or mixtures thereof, wherein the formulations exhibit reduced viscosity or improved stability relative to excipient-free controls. In exemplary embodiments, the therapeutic protein is at a high protein concentration as described above. In some embodiments, the excipient is present at a viscosity-reducing (weight:volume) concentration; in other embodiments, the excipient is present at an aggregation-reducing concentration. Any of these excipients can be used at concentrations up to their solubility limit. Such solutions may further comprise a sugar or other polyol such as sucrose or sorbitol, in an amount effective to further improve stability, reduce aggregation, and/or make the formulation isotonic, without significantly increasing viscosity.

In exemplary embodiments, the concentration of creatine/creatinine is about 10 µM to about 300 mM, or about 10 µM to about 50 mM, or about 1 µM to about 750 mM. In exemplary embodiments the concentration of creatine/creatinine is at least about 1, 2, 3, 4, 5, 6, 7, 8, 9, 10, 25, 50, 75, 100, 250, 500, or 750 µM. In further exemplary embodiments the concentration of creatine/creatinine is at least about 1, 2, 3, 4, 5, 6, 8, 10, 15, 20, 25, 30, 35, 40, 45, 50, 60, 70, 75, or 100 mM. In any of the preceding embodiments the concentration of creatine/creatinine is up to about 50, 75, 100, 150, 200, 250, 300, 350, 400, 450, 500, 550, 600, 650, 700 or 750 mM.

In other exemplary embodiments, the concentration of carnitine is about 5 to about 300 mM, or about 25 to about 400 mM, or about 100 to about 300 mM. In further exemplary embodiments, the concentration of carnitine is at least about 5, 10, 15, 20, 25, 30, 35, 40, 45, 50, 75, or 100 mM, and/or up to about 100, 150, 200, 250, 300, 350, 400, 450, 500, 550, 600, 650, 700, 750, 800, 850, 900, or 950 mM, or 1, 1.5, 2, 2.5, or 3 M.

In another aspect, the invention provides lyophilized protein formulations comprising a therapeutic protein and an excipient selected from the group consisting of creatinine, creatine or carnitine, or mixtures thereof, wherein upon reconstitution with the recommended amount of diluent, the formulations exhibit reduced viscosity relative to excipient-free controls. In exemplary embodiments, the therapeutic protein is at a high protein concentration as described above. In some embodiments, the excipient is present at an amount effective to reduce viscosity upon reconstitution with diluent (weight:weight concentration); in other embodiments the excipient is present at an aggregation-reducing (weight:weight) concentration. Such formulations may further comprise a sugar or other polyol such as sucrose or sorbitol, in an amount effective to further improve stability, reduce aggregation, and/or make the formulation isotonic, without significantly increasing viscosity.

In exemplary embodiments, the concentration of creatine/creatinine is at least about 4 ng per mg therapeutic protein, up to about 1.25 mg per mg therapeutic protein. In some embodiments, the concentration of creatine/creatinine is at least about 4, 10, 25, 50, 75, 100, 250, 500, or 750 ng per mg therapeutic protein. In yet other embodiments, the concentration of creatine/creatinine is at least about 1, 5, 10, 20, 30, 40, 50, 60, 70, 80, 90 or 100 µg per mg therapeutic protein. In any of the preceding embodiments, the concentration of creatine/creatinine is up to about 150, 200, 250, 300, 350, 400, 450, 500, 550, 600, 650, 700, 750, 800, 850, 900, 950, 1000 or 1250 µg per mg therapeutic protein.

In other exemplary embodiments, the concentration of carnitine is at least about 2 µg per mg therapeutic protein, up to about 7 mg per mg therapeutic protein. In some embodiments, the concentration of carnitine is at least about 5, 10, 15, 20, 25, 30, 35, 40, 45, or 50 µg per mg therapeutic protein. In any of the preceding embodiments, the concentration of carnitine can be up to about 400, 450, 500, 550, 600, 650, 700, 750, 800, 850, 900, or 950 µg or up to about 1, 2, 3, 4, 5, 6, or 7 mg per mg therapeutic protein.

In yet another embodiment, the present invention provides a method of preventing self-association of proteins in liquid formulations by using creatine/creatinine or carnitine as excipients in any of the amounts or concentrations described herein. Formulations with improved stability (e.g., reduced aggregation) and shelf-life are also provided.

The invention also provides a kit comprising a liquid protein formulation of the invention, and instructions for its administration, optionally with a container, syringe and/or other administration device. The invention further provides a kit comprising a lyophilized protein formulation of the invention, optionally in a container, and instructions for its reconstitution and administration, optionally with a vial of sterile diluent, and optionally with a syringe or other administration device. Exemplary containers include vials, tubes, bottles, single or multi-chambered pre-filled syringes, or cartridges. Exemplary administration devices include syringes, with or without needles, infusion pumps, jet injectors, pen devices, transermal injectors, or other needle-free injector, or an aerosolization device for nasal or pulmonary delivery.

Assessing Viscosity or Stability

In another aspect, a method is provided for screening for a viscosity-reducing concentration of excipient comprising the steps of: (1) assessing the viscosity of a first solution comprising a first concentration of excipient(s) selected from the group consisting of creatinine, creatine, carnitine and mixtures thereof, and a therapeutic protein, such as an antibody, (2) assessing the viscosity of a second solution comprising a different second concentration of the excipient(s) and the therapeutic protein, and (3) determining that the first concentration of excipient(s) is more viscosity-reducing than the second concentration of excipient if the first solution is less viscous. Viscosity can be determined, e.g., using a Brookfield RV-DVIII Rheometer which is stabilized at 25° C. with a circulating temperature bath. Five hundred microliters of sample is pipetted into the rheometer and the rpm adjusted for percentage torque values between 10-80%. The samples are allowed to stabilize at that range and data points are collected.

Similar methods are provided for screening for an aggregation-reducing or stabilizing concentration of excipient.

Stability can be assessed in many ways, including monitoring conformational change over a range of temperatures (thermostability) and/or time periods (shelf-life) and/or after exposure to stressful handling situations (e.g. physical shaking). Stability of formulations containing varying concentrations of formulation components can be measured using a variety of methods. For example, the amount of protein aggregation can be measured by visual observation of turbidity, by measuring absorbance at a specific wavelength, by size exclusion chromatography (in which aggregates of a protein will elute in different fractions compared to the protein in its native active state), HPLC, or other chromatographic methods. Other methods of measuring conformational change can be used, including using differential scanning calorimetry (DSC), e.g. to determine the temperature of denaturation, or circular dichroism (CD), which measures the molar ellipticity of the protein. Fluorescence can also be used to analyze the composition. Fluorescence encompasses the release or absorption of energy in the form of light or heat, and changes in the polar properties of light. Fluorescence emission can be intrinsic to a protein or can be due to a fluorescence reporter molecule. For example, ANS is a fluorescent probe that binds to the hydrophobic pockets of partially unfolded proteins. As the concentration of unfolded protein increases, the number of hydrophobic pockets increases and subsequently the concentration of ANS that can bind increases. This increase in ANS binding can be monitored by detection of the fluorescence signal of a protein sample. Other means for measuring stability can be used and are well known to persons of skill in the art.

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Example 1

The effects of protein concentration on the viscosity of antibody formulations containing Antibody A, an IgG1 antibody, at pH 5-5.2 were studied. First, 70 mg/ml Antibody A was formulated in 10 mM Sodium Acetate 9% Sucrose pH 5.20 and was dialyzed against 4 liters of 10 mM Na Acetate pH 5.20. Dialysis was carried out at 4° C. overnight using 10,000 MWCO snakeskin pleated dialysis tubing. Next, Antibody A was filtered through a 0.22 μm cellulose acetate filter. The protein was concentrated by subjecting to centrifugation with Amicon Ultra regenerated cellulose filter (100,000 MWCO) at 3500 rpm for 2-3 hours at 20° C. The protein was collected from the filter into 15 ml Falcon tubes and mixed by inversion. Protein concentration was determined by spectrophotometry and the concentration was adjusted to 235 mg/ml. Samples were vortexed for 10 seconds and then allowed to sit for 1 hour at least (in order to equilibrate to room temperature and outgas bubbles). A Brookfield RV-DVIII Rheometer was turned on and the temperature stabilized at 25° C. with a circulating temperature bath. Five hundred microliters of sample was pipetted into the rheometer and the rpm was adjusted to get percentage torque values between 10-80%. The samples were allowed to stabilize at that range and data points were collected.

Example 2

The formulation of Example 1 was used to determine whether the concentrations of creatine and creatinine remain stable at equilibrium over time. As can be seen in FIG. 1, a 275 mM creatine/creatinine formulation will contain 225 mM creatinine+50 mM creatine at equilibrium at pH 5.20. Furthermore, these concentrations remain steady over the course of two weeks at a temperature of 80° C., indicating that the excipients are highly stable in solution.

Example 3

In order to confirm that, at equilibrium, the amounts of creatine/creatinine present in the formulation are identical whether starting with either creatine or creatinine, a formulation was made with each as starting material. First, 70 mg/ml Antibody A was formulated in 10 mM Sodium Acetate 9% Sucrose pH 5.20 and was dialyzed against 4 liters of 10 mM Na Acetate pH 5.20. Dialysis was carried out at 4° C. overnight using 10,000 MWCO snakeskin pleated dialysis tubing. Next, Antibody A was filtered through a 0.22 μm cellulose acetate filter. The dialyzed Antibody A was formulated to 50 mM creatine and 50 mM creatinine in 15 mL conical tubes. The protein was concentrated by subjecting to centrifugation with Amicon Ultra regenerated cellulose filter (100,000 MWCO) at 3500 rpm for 2-3 hours at 20° C. The protein was collected from the filter into 15 ml Falcon tubes and mixed by inversion. Protein concentration was determined by spectrophotometry and the concentration was adjusted to 235 mg/ml. Samples were vortexed for 10 seconds and then allowed to sit for 1 hour at least (in order to equilibrate to room temperature and outgas bubbles). A Brookfield RV-DVIII Rheometer was turned on and the temperature stabilized at 25° C. with a circulating temperature bath. Five hundred microliters of sample was pipetted into the rheometer and the rpm was adjusted to get percentage torque values between 10-80%. The samples were allowed to stabilize at that range and data points were collected. As can be seen in FIG. 2, the reduction in viscosity of the formulation is the same regardless of whether one begins with 50 mM creatine or creatinine. In either case, the reduction in viscosity of the formulation is shown to be approximately 30%.

Example 4

Figure 3:
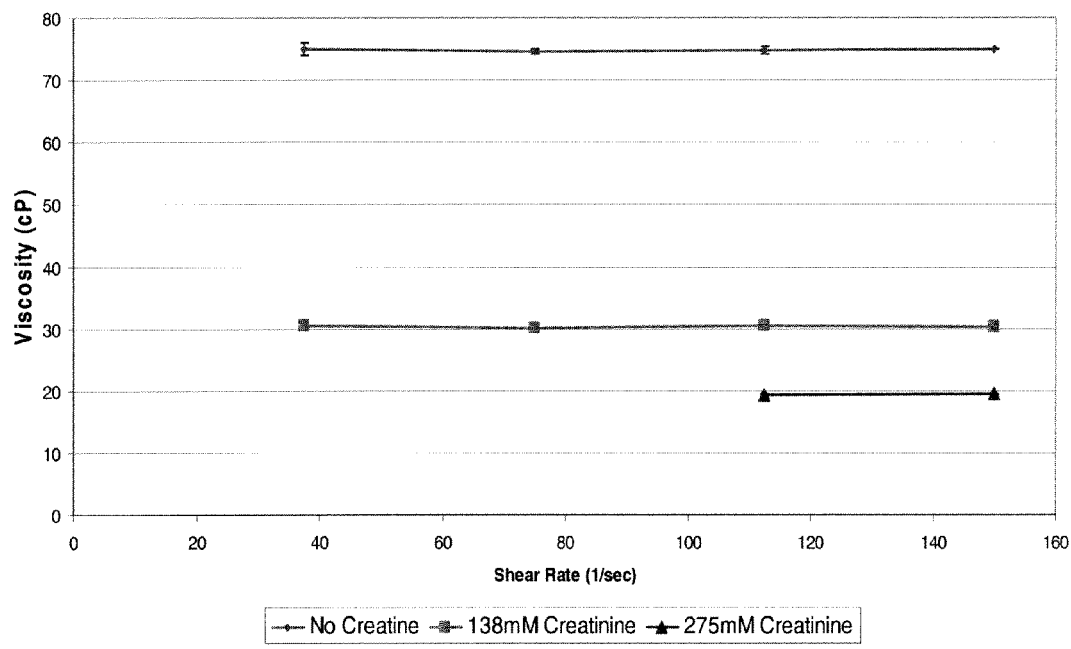
FIG. 3. Increasing concentrations of creatinine lead to a further decrease in viscosity of a formulation containing 236 mg/ml Antibody A in 10 mM sodium acetate pH 5.20. At 275 mM creatinine at pH 5.20, there will be 225 mM creatinine and 50 mM creatine at equilibrium. At that concentration, the formulation is approximately 75% less viscous than the control formulation.

The effects of increasing the concentration of excipient in pharmaceutical formulations was tested, and the results are shown in FIG. 3. First, 70 mg/ml Antibody A was formulated in 10 mM Sodium Acetate 9% Sucrose pH 5.20 and was dialyzed against 4 liters of 10 mM Na Acetate pH 5.20. Dialysis was carried out at 4° C. overnight using 10,000 MWCO snakeskin pleated dialysis tubing. Next, Antibody A was filtered through a 0.22 μm cellulose acetate filter. The protein was concentrated by subjecting to centrifugation with Amicon Ultra regenerated cellulose filter (100,000 MWCO) at 3500 rpm for 2-3 hours at 20° C. The protein was collected from the filter into 15 ml Falcon tubes and mixed by inversion.

To get 138 mM creatinine 500 μl of Antibody A/275 mM creatinine was mixed with 500 μl Antibody A control. Mixture was vortexed for 10 seconds and then the samples were allowed to sit for 1 hour at least (in order to equilibrate to room temperature and outgas bubbles). A Brookfield RV-DVIII Rheometer was turned on and the temperature stabilized at 25° C. with a circulating temperature bath. Five hundred microliters of sample was pipetted into the rheometer and the rpm was adjusted to get percentage torque values between 10-80%. The samples were allowed to stabilize at that range and data points were collected. The reduction in viscosity is seen to be directly proportional to the concentration of excipient used, with the viscosity being reduced by approximately 75% when a starting concentration of 275 mM creatinine (225 mM creatinine/50 mM creatine at equilibrium) was used.

Example 5

As a method to determine the effective concentration range of creatinine in pharmaceutical formulations, a titration analysis was done using concentrations ranging from 0-50 mM creatinine. First, 70 mg/ml Antibody A was formulated in 10 mM Sodium Acetate 9% Sucrose pH 5.20 and was dialyzed against 4 liters of 10 mM Na Acetate pH 5.20. Dialysis was carried out at 4° C. overnight using 10,000 MWCO snakeskin pleated dialysis tubing. Next, Antibody A was filtered through a 0.22 μm cellulose acetate filter. The protein was concentrated by subjecting to centrifugation with Amicon Ultra regenerated cellulose filter (100,000 MWCO) at 3500 rpm for 2-3 hours at 20° C. The protein was collected from the filter into 15 ml Falcon tubes and mixed by inversion. Nine hundred and fifty microliters of concentrated Antibody A was mixed with 50 μl of creatinine at varying concentrations. Final creatinine concentrations ranged from 50-1 mM creatinine. Mixture was vortexed for 10 seconds and then the samples were allowed to sit for 1 hour at least (in order to equilibrate to room temperature and outgas bubbles). A Brookfield RV-DVIII Rheometer was turned on and the temperature stabilized at 25° C. with a circulating temperature bath. Five hundred microliters of sample was pipetted into the rheometer and the rpm was adjusted to get percentage torque values between 10-80%. The samples were allowed to stabilize at that range and data points were collected. The results from the experiment can be seen in FIG. 4. Again, the analysis confirms that formulation viscosity is reduced in a linear fashion with respect to increasing concentrations of excipient.

Example 6

Figure 5:
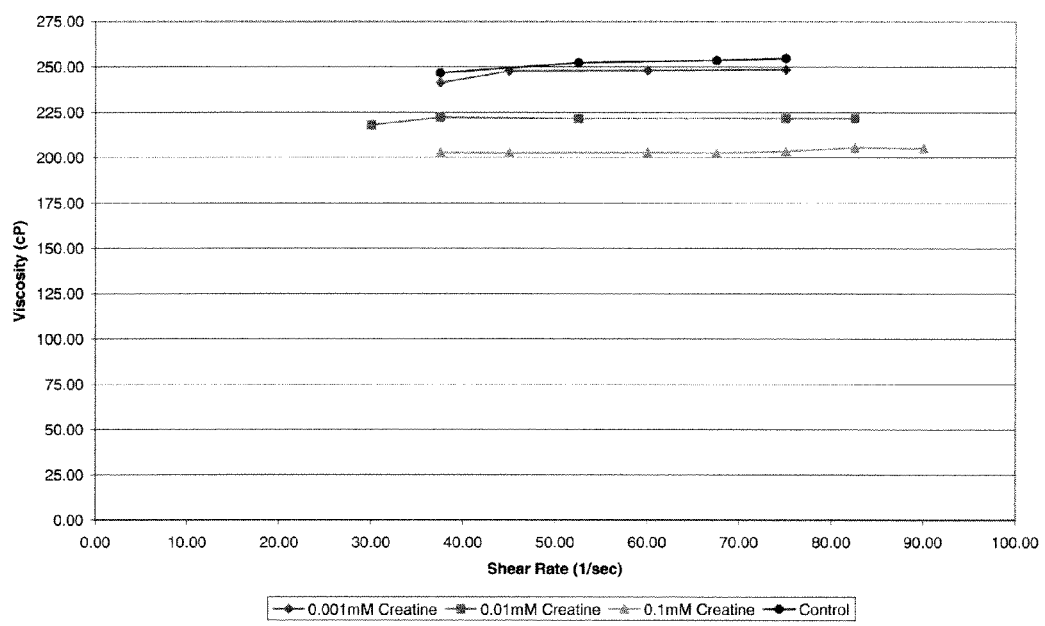
FIG. 5. Effect of varying creatinine/creatine concentrations on viscosity of a formulation containing 300 mg/ml Antibody A.

First, 70 mg/ml Antibody A was formulated in 10 mM Sodium Acetate 9% Sucrose pH 5.20 and was dialyzed against 4 liters of 10 mM Na Acetate pH 5.20. Dialysis was carried out at 4° C. overnight using 10,000 MWCO snakeskin pleated dialysis tubing. Next, Antibody A was filtered through a 0.22 μm cellulose acetate filter. The protein was collected from the filter into 15 ml Falcon tubes and mixed by inversion. Nine-hundred fifty microliters of concentrated Antibody A was mixed with 50 μl of creatine at varying concentrations. Final creatine concentrations ranged from 0.001-0.1 mM creatine. Mixture was vortexed for 10 seconds and then the samples were allowed to sit for at least 1 hour to equilibrate to room temperature and reduce bubbles. A Brookfield RV-DVIII Rheometer was turned on and the temperature stabilized at 25° C. with a circulating temperature bath. Five hundred microliters of sample was pipetted into the rheometer and the rpm was adjusted to get percentage torque values between 10-80%. The samples were allowed to stabilize at that range and data points were collected. Results of the experiment are shown in FIG. 5. Concentrations of creatine down to 10 μm are effective at reducing the viscosity of the formulation by at least 10%. At 100 μm the viscosity of the formulation is reduced by 25% relative to control formulations.

Example 7

Figure 6:
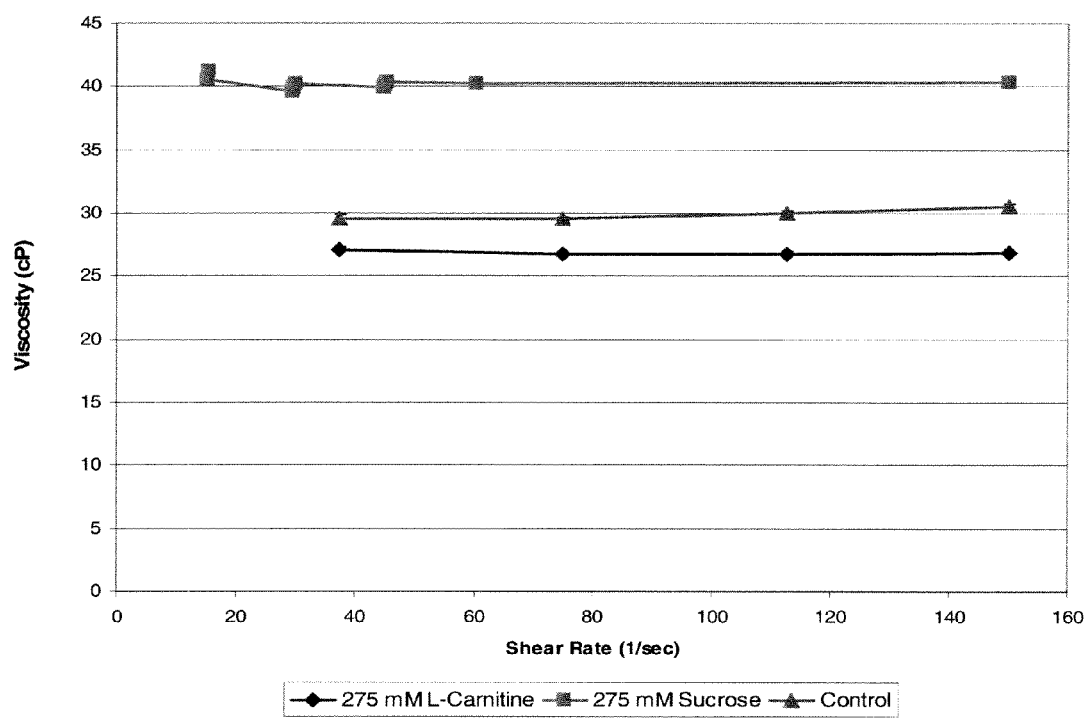
FIG. 6. Carnitine decreases the viscosity of a formulation of 215 mg/ml of Antibody A in 10 mM sodium acetate pH 5.0.

To test the effects of carnitine on pharmaceutical formulations with a high protein concentration, a formulation at pH 5.0 containing 215 mg/ml of Antibody A with 275 mM carnitine was tested for its effects on viscosity. First, 70 mg/ml Antibody A was formulated in 10 mM Sodium Acetate 9% Sucrose pH 5.20 and was dialyzed against 4 liters of 10 mM Na Acetate pH 5.20. Dialysis was carried out at 4° C. overnight using 10,000 MWCO snakeskin pleated dialysis tubing. Next, Antibody A was filtered through a 0.22 μm cellulose acetate filter. The protein was concentrated by subjecting to centrifugation with Amicon Ultra regenerated cellulose filter (100,000 MWCO) at 3500 rpm for 2-3 hours at 20° C. The protein was collected from the filter into 15 ml Falcon tubes and mixed by inversion. One thousand microliters of concentrated Antibody A was mixed with solid L-Carnitine and sucrose. Final L-Carnitine and sucrose concentration was 275 mM L-Carnitine and 275 mM sucrose. The mixture was vortexed until the L-Carnitine and sucrose had completely gone into solution Mixture was vortexed for 10 seconds and then the samples were allowed to sit for 1 hour at least (in order to equilibrate to room temperature and outgas bubbles). A Brookfield RV-DVIII Rheometer was turned on and the temperature stabilized at 25° C. with a circulating temperature bath. Five hundred microliters of sample was pipetted into the rheometer and the rpm was adjusted to get percentage torque values between 10-80%. The samples were allowed to stabilize at that range and data points were collected. FIG. 6 shows that the decrease in viscosity of the formulation was 10% relative to excipient-free control, but 35% relative to other isotonic formulations containing a different excipients such as sucrose.

Example 8

Figure 7:
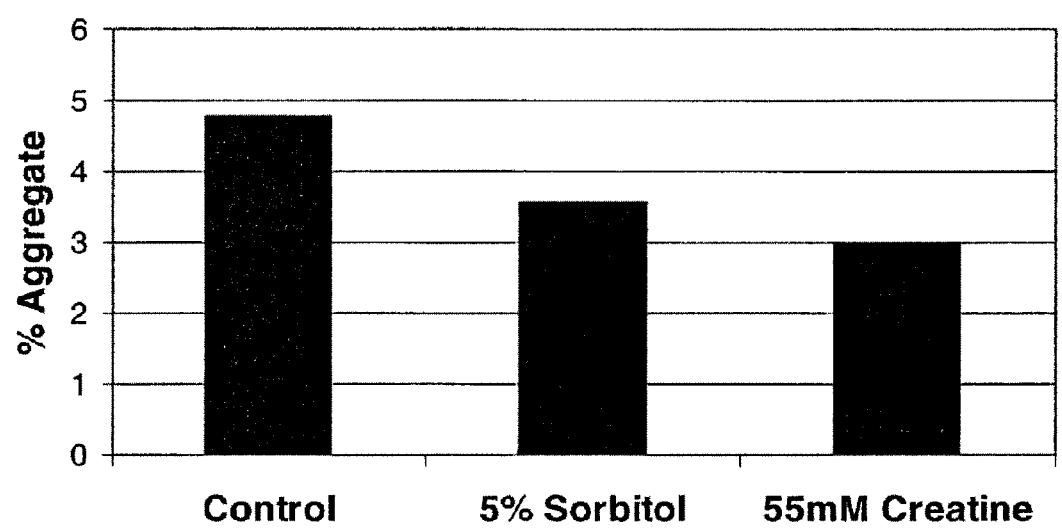
FIG. 7. The effect of creatine on thermally induced aggregation of Antibody A. A concentration of 55 mM creatine was tested for its ability to reduce thermally induced aggregation when the formulation was maintained at 52° C.

The effect of creatine on protein stability was assessed by its addition to protein formulations in concentrations as high as 55 mM. Antibody A bulk (70 mg/mL) in 10 mM Sodium Acetate 9% Sucrose pH 5.20 was dialyzed against 10 mM Sodium Acetate pH 5.00 overnight at 4° C. Dialyzed protein was then concentrated by centrifugation using Amicon Ultra 10,000 MWCO centrifugal concentrators at 3,000 rpm using a Beckman Coulter Allegra X12-R centrifuge. The concentrated Antibody A (230 mg/mL) was then diluted to 100 mg/mL in 10 mM sodium acetate, 10 mM sodium acetate containing 10% sorbitol, or 10 mM sodium acetate containing 100 mM creatine to reach the final excipient concentrations. Samples were sterile filtered and filled in 3 cc glass vials in a sterile hood. Samples were stored for 8 days in a 52° C. incubator before analysis by Size-Exclusion Chromatography (SEC-HPLC). FIG. 7 shows the effect of creatine on the reduction in antibody aggregation during incubation for eight days at 52° C. At 52° C., 55 mM creatine is more effective at preventing Antibody A (100 mg/mL) aggregation than 5% sorbitol, another excipient.

Example 9

Figure 8:
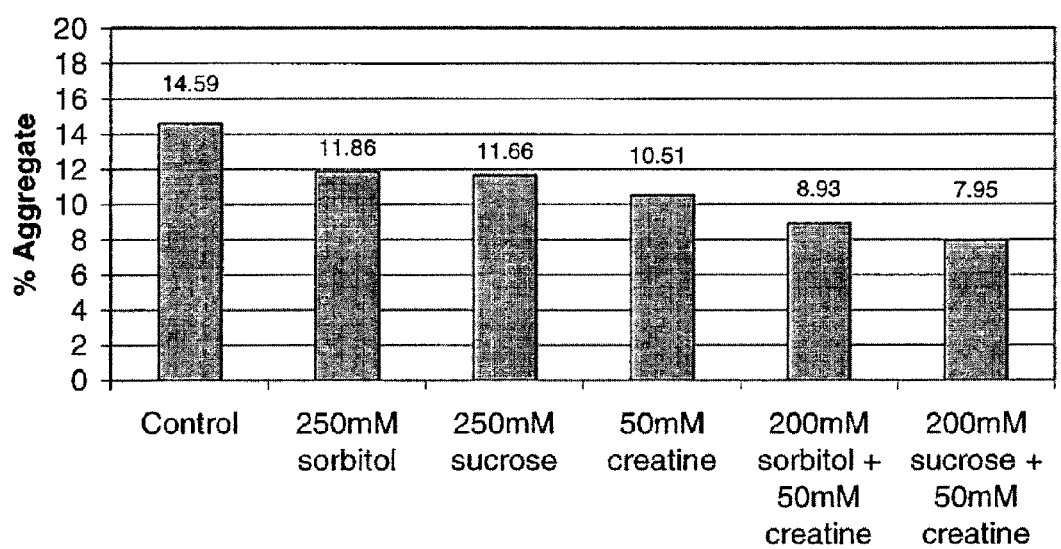
FIG. 8. The effect of creatine-polyol combinations on thermally induced aggregation of Antibody A.

Testing the effects of creatine-polyol combinations on thermally induced aggregation of Antibody A. Combinations of creatine and either sucrose or sorbitol were tested for the ability to reduce aggregation of Antibody A (150 mg/mL) after two weeks at 52° C. Antibody A (200 mg/mL) in 20 mM sodium acetate pH 5.00 was dialyzed into 20 mM sodium acetate pH 5.00 containing 250 mM sorbitol, 250 mM sucrose, 50 mM creatine, 200 mM sorbitol+50 mM creatine, and 200 mM sucrose+50 mM creatine. Following overnight dialysis, Antibody A concentration was checked by measuring absorbance at 280 nM using a UV-Vis spectrophotometer. Concentrations of each formulation were adjusted to 150 mg/mL by adding the corresponding formulation buffer for each sample. Samples were sterile filtered and filled in 3 cc glass vials in a sterile hood. Samples were stored for 2 weeks in a 52° C. incubator before analysis by Size-Exclusion Chromatography (SEC-HPLC). The results of the experiment are shown in FIG. 8, and demonstrate that the combination of creatine with either sorbitol or sucrose leads to a greater reduction in Antibody A aggregation than with any of the excipients alone. Using 200 mM sucrose plus 50 mM creatine yields an approximate 2-fold reduction in the percent aggregation of the antibody formulation after two weeks at 52° C.

Example 10

Figure 9:
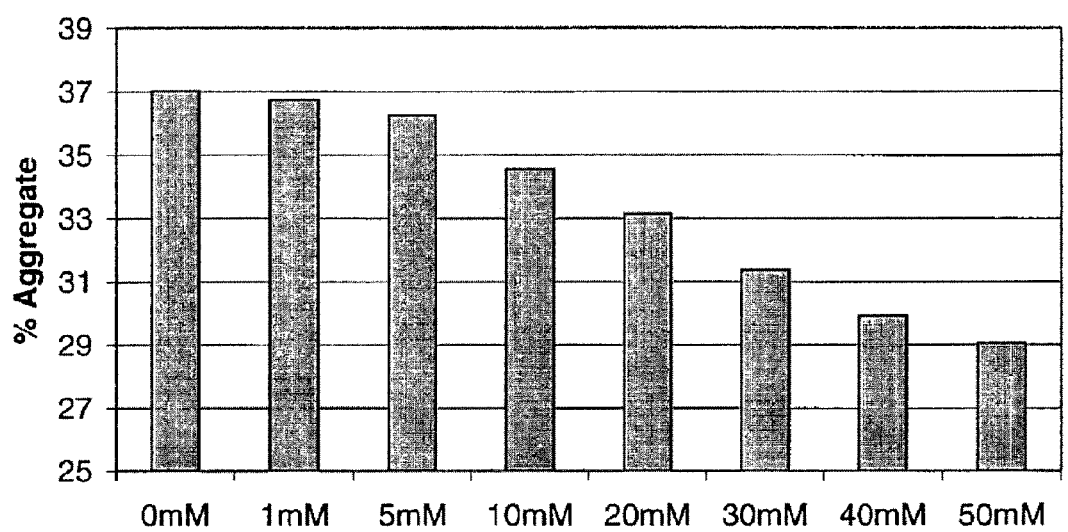
FIG. 9. The effect of creatine concentration on reducing thermally induced aggregation of an anti-streptavidin IgG2 antibody, at a concentration of 30 mg/ml, at 52° C. for one week.

The effect of creatine concentration on $IgG_2$ antibody (30 mg/mL) aggregation at 52° C. for one week was tested using an anti-streptavidin antibody. Anti-streptavidin IgG2 MAb (30 mg/mL) in 20 mM sodium acetate, 5% Sorbitol pH 5.00 was dialyzed against 20 mM sodium acetate pH 5.00 overnight at 4° C. Dialyzed protein was then concentrated to 60 mg/mL by centrifugation using Amicon Ultra 10,000 MWCO centrifugal concentrators at 3,000 rpm using a Beckman Coulter Allegra X12-R centrifuge. Samples were then diluted to 30 mg/mL using different ratios of 20 mM sodium acetate pH 5.00 and 20 mM sodium acetate pH 5.00 containing 100 mM creatine. Samples were sterile filtered and filled in 3 cc glass vials in a sterile hood. Samples were stored for 1 week in a 52° C. incubator before analysis by Size-Exclusion Chromatography (SEC-HPLC). The results in FIG. 9 show the effect of creatine on the reduction in anti-streptavidin aggregation. Creatine concentration appears to have a linear effect on reduction of antibody aggregation from 0 mM to 50 mM creatine. As little as 1 mM creatine has a detectable effect on antibody aggregation.

Example 11

Figure 10:
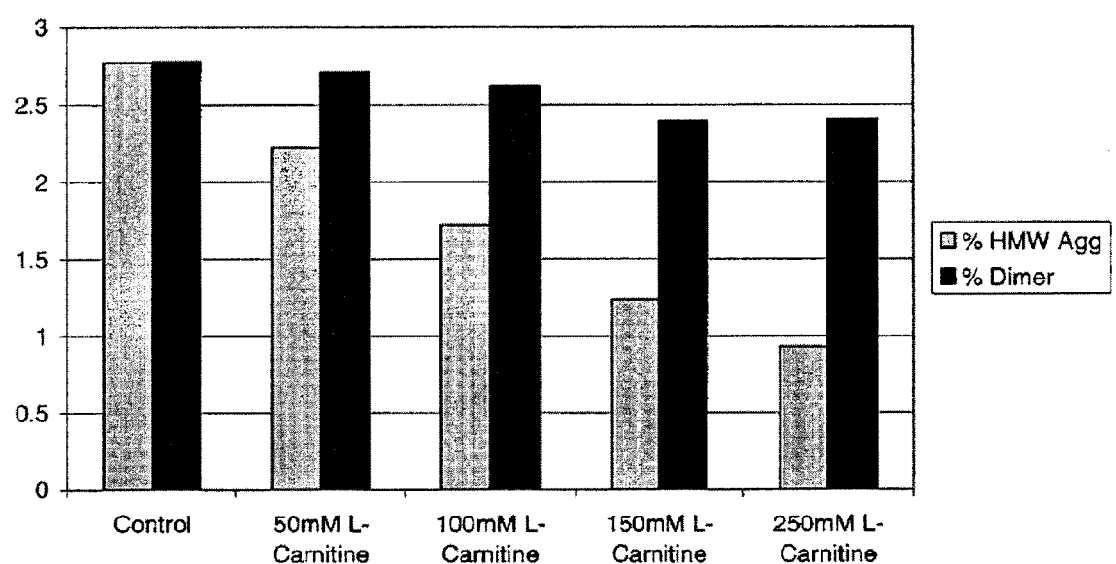
FIG. 10. The effect of L-carnitine concentration on reduction of thermally induced aggregation of Antibody A, at a concentration of 100 mg/ml, at 52° C. for four days.

The effect of L-carnitine concentration on reduction of thermally induced aggregation of Antibody A was tested. Antibody A bulk (70 mg/mL) in 10 mM sodium acetate 9% sucrose pH 5.20 was dialyzed against 10 mM sodium acetate pH 5.00 overnight at 4° C. Dialyzed protein was then concentrated by centrifugation using Amicon Ultra 10,000 MWCO centrifugal concentrators at 3,000 rpm using a Beckman Coulter Allegra X12-R centrifuge. The concentrated Antibody A (230 mg/mL) was then diluted to 100 mg/mL varying ratios of 10 mM sodium acetate pH 5.00 and 10 mM sodium acetate pH 5.00 containing 500 mM L-Carnitine. Samples were sterile filtered and filled in 3 cc glass vials in a sterile hood. Samples were stored for 4 days in a 52° C. incubator before analysis by Size-Exclusion Chromatography (SEC-HPLC). FIG. 10 shows the effect of increasing concentrations of L-carnitine on aggregation of a solution of 100 mg/mL Antibody A, after maintaining the formulation at 52° C. for four days. The data show that increasing concentrations of L-carnitine have a linear effect on the reduction in high molecular weight aggregates. There was also a reduction in dimer formation, but the effect on high molecular weight aggregates was much more pronounced.

Example 12

Figure 11:
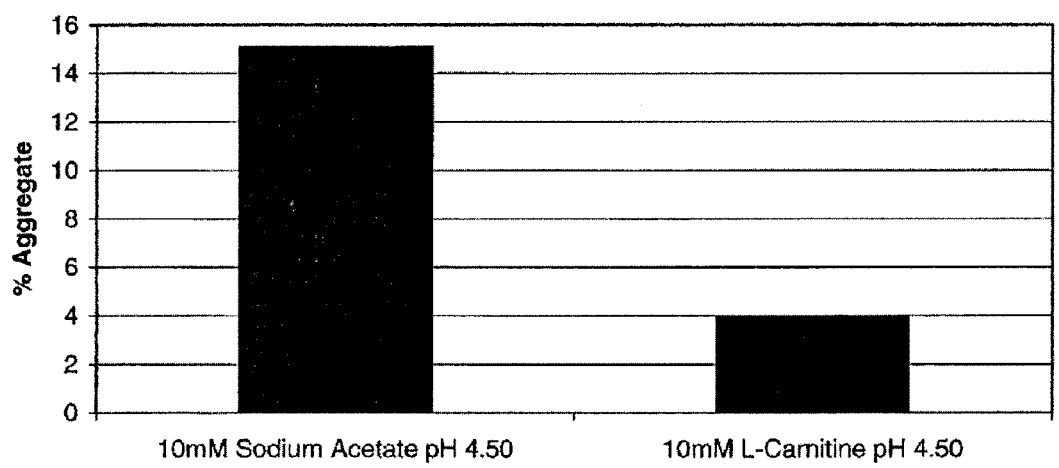
FIG. 11. The effect of an L-carnitine buffered formulation on thermally induced aggregation of another IgG2 antibody, at a concentration of 7 mg/mL, at 52° C. for four weeks.

The effect of an L-carnitine buffered formulation on thermally induced aggregation of Antibody B, an IgG2 antibody, was tested. Antibody B bulk (70 mg/mL) in 10 mM sodium acetate 5% sorbitol pH 5.00 was dialyzed into deionized water over at 4° C. The resulting antibody solution was diluted ten-fold to 7 mg/mL in either 10 mM sodium acetate pH 4.50 or 10 mM L-carnitine pH 4.50. pH of each sample was confirmed using a pH meter. Samples were sterile filtered and filled in 3 cc glass vials in a sterile hood. Samples were stored for 4 weeks in a 52° C. incubator before analysis by Size-Exclusion Chromatography (SEC-HPLC). Because L-carnitine has an ionizable carboxylic acid group with a pKa of 3.8, it can function as a buffer in aqueous formulations between pH 2.8-4.8. The pH range from 4-4.8 may be useful for antibodies and other proteins that are more stable at lower pH. Results in FIG. 11 show that L-carnitine buffered antibody formulations in this pH range are less prone to aggregation than acetate buffered formulations, as seen by an almost 4-fold reduction in aggregation.

Example 13

Figure 12:
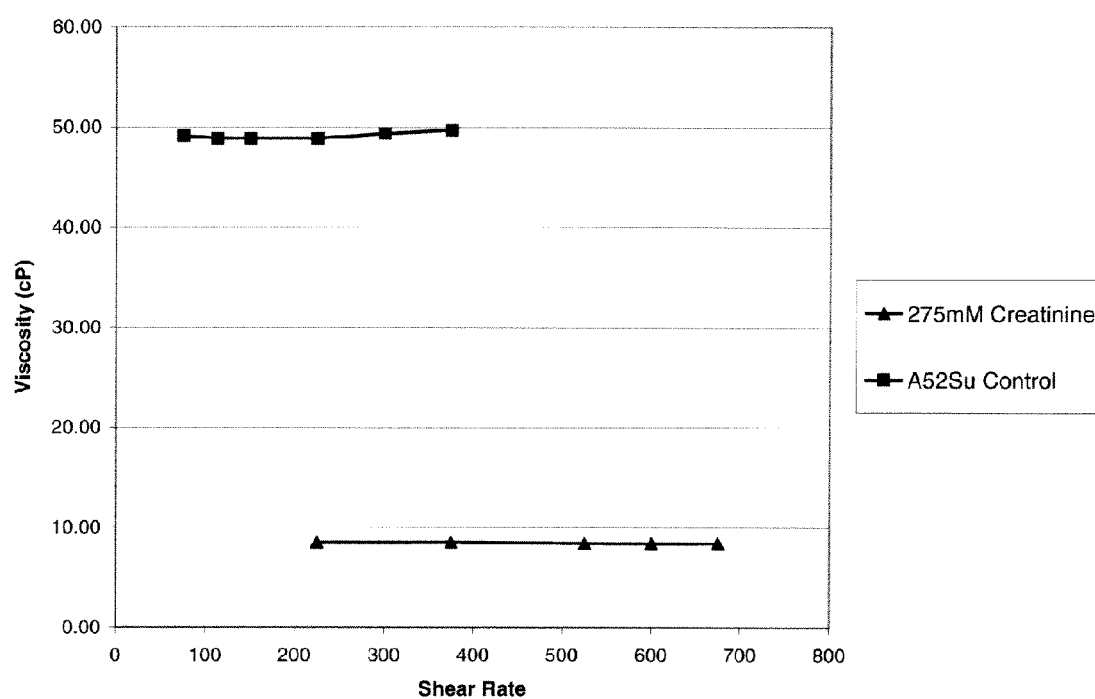
FIG. 12. The effect of creatinine on the viscosity of a humanized IgG2 antibody formulation at a concentration of 160 mg/mL 10 mM Sodium Acetate pH 5.20. "A52Su Control" is sodium acetate pH 5.20 containing 9% sucrose.

The effects of creatinine on the viscosity of a humanized IgG2 antibody formulation is shown in FIG. 12. Samples were dialyzed overnight at 4° C. against 4 liters of 10 mM sodium acetate pH 5.20 containing either 275 mM creatinine or 9% sucrose. Samples were then concentrated using Amicon Ultra (100,000 MWCO) centrifugal concentrators at 3500 rpm for approximately 5 hours at 20° C. Protein concentrations were measured by UV absorbance at 280 nm using diluted protein solutions prepared using positive displacement pipettes. Protein concentrations were adjusted to 160 mg/mL by diluting with the appropriate formulation buffer. Viscosity of the samples was measured using a Brookfield RV-DVIII Rheometer. Five hundred microliters of sample was pipetted into the rheometer and the rpm was adjusted to get percentage torque values between 10-80%. The samples were allowed to stabilize at that range and data points were collected. The results shown in FIG. 12 show that the sample containing 275 mM creatinine is more than 80% less viscous than the sample containing 9% sucrose.

What is claimed is:

1. A method for reducing the viscosity of a liquid pharmaceutical formulation comprising a therapeutic protein at a concentration of at least 70 mg/ml, consisting of the step of combining the therapeutic protein with a viscosity-reducing concentration of an excipient selected from the group consisting of creatine, creatinine, and mixtures thereof.

2. The method of claim 1 wherein viscosity of the formulation is reduced by at least 10%.

3. The method of claim 1 wherein viscosity of the formulation is reduced by at least 30%.

4. A method of reducing the viscosity of a liquid pharmaceutical formulation consisting of a therapeutic protein at a concentration of at least 70 mg/ml in acetate buffer consisting of the step of combining the therapeutic protein with a viscosity-reducing concentration of an excipient selected from the group consisting of creatine, creatinine, carnitine and mixtures thereof.

5. The method of claim 4 wherein the viscosity of the formulation is reduced by at least 10%.

6. The method of claim 4 wherein the viscosity of the formulation is reduced by at least 30%.

* * * * *